(12) United States Patent
Brown et al.

(10) Patent No.: US 7,544,466 B1
(45) Date of Patent: Jun. 9, 2009

(54) GHRELIN O-ACYLTRANSFERASE (GOAT) BIOCHEMICAL ASSAY

(75) Inventors: Michael S. Brown, Dallas, TX (US); Joseph L. Goldstein, Dallas, TX (US); Nick V. Grishin, Dallas, TX (US); Jing Yang, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/967,171

(22) Filed: Dec. 29, 2007

(51) Int. Cl.
*C12Q 1/00* (2006.01)
*G01N 33/53* (2006.01)
*C12N 9/00* (2006.01)
*C12N 9/10* (2006.01)
*C07H 21/04* (2006.01)

(52) U.S. Cl. .............................. 435/4; 435/7.5; 435/7.9; 435/183; 435/193; 536/23.2

(58) Field of Classification Search ................... None
See application file for complete search history.

(56) References Cited

FOREIGN PATENT DOCUMENTS

WO    WO 2008/079705    7/2008

OTHER PUBLICATIONS

Chica et al. Curr Opin Biotechnol. Aug. 2005;16(4):378-84.*
Sen et al. Appl Biochem Biotechnol. Dec 2007;143(3):212-23.*

* cited by examiner

*Primary Examiner*—Christian L Fronda
(74) *Attorney, Agent, or Firm*—Richard Aron Osman

(57) ABSTRACT

Ghrelin is acylated by ghrelin O-acyltransferase. Ghrelin O-acyltransferase assays comprise contacting a mixture of ghrelin and recombinant ghrelin O-acyltransferase with an agent; and detecting a resultant decrease in acylation of the ghrelin by the acyltransferase.

16 Claims, No Drawings

SEQUENCE LISTING

<160> NUMBER OF SEQ ID NOS: 28

<210> SEQ ID NO 1
<211> LENGTH: 1372
<212> TYPE: DNA
<213> ORGANISM: mouse

<400> SEQUENCE: 1

```
gacttcccctt  ttacaagggc  accgcttagg  gactctagga  aggacagtgg  gcctcacatt    60
caggatggat  tggctccagc  tctttttct   gcatccttta  tcattttatc  aaggggctgc   120
attccccttt  gcgcttctgt  ttaattatct  ctgcatcttg  dacaccttt   ccacccgggc   180
caggtacctc  tttctcctgg  ctggaggagg  tgtcctggct  tttgctgcca  tgggtcccta   240
ctctctgctc  atcttcatcc  ctgcgctctg  cgctgtggct  ctggtctcct  tcctcagtcc   300
acaggaagtc  cataggctga  ccttcttctt  tcagatgggc  tggcagaccc  tgtgccatct   360
gggtcttcac  tacaccgaat  actacctggg  tgagcctcca  ccgtgaggt   tctacatcac   420
tctttcttcc  ctcatgctct  tgacgcagag  agtcacatcc  ctctcactgg  acatttgtga   480
agggaaggtg  gaggccccga  ggcggggcat  caggagcaag  agttctttct  ctgagcacct   540
gtgggatgct  ctacctcatt  tcagctactt  gctctttttc  cctgctctcc  tgggaggctc   600
cctgtgttcc  ttccggaggt  ttcaggcttg  cgttcaaaga  tcaagctctt  tgtatccgag   660
tatctctttt  cgggctctga  cctggagggg  tctgcagatt  ctcgggctgg  agtgcctcaa   720
ggtggcgctg  aggagcgcgg  tgagtgctgg  agctggactg  gatgactgcc  agcggctgga   780
gtgcatctac  ctcatgtggt  ccacagcctg  gctctttaaa  ctcacctatt  actcccattg   840
gatcctggac  gactctctcc  tccacgcggc  gggcttggc   gctgaggctg  gccaggggcc   900
tggagaggag  ggatacgtcc  ccgacgtgga  catttggacc  ctggaaacta  cccacaggat   960
ctccctgttc  gccaggcagt  ggaaccgaag  cacagctctg  tggctcagga  ggctcgtctt  1020
ccggaagagc  cggcgctggc  ccctgctgca  gacatttgcc  ttctctgcct  ggtggcacgg  1080
```

```
gctccaccca ggtcaggtgt tcggcttcct gtgctggtct gtaatggtga aagccgatta    1140
tctgattcac acttttgcca acgtatgtat cagatcctgg ccctgcggc tgctttatag    1200 agccctcact tgggctcata cccaacctcat cattgcctac atcatgctgg cggtggaggg    1260
ccggagcctt tcctctctct gccaactgtg ctgttcttac aacagtctct tccctgtgat    1320
gtacggtctt ttgcttttc tgttagcgga gagaaaagac aaacgtaact ga            1372
```

<210> SEQ ID NO 2
<211> LENGTH: 435
<212> TYPE: PRT
<213> ORGANISM: mouse

<400> SEQUENCE: 2

```
Met Asp Trp Leu Gln Leu Phe Phe Leu His Pro Leu Ser Phe Tyr Gln
1               5                   10                  15

Gly Ala Ala Phe Pro Phe Ala Leu Leu Phe Asn Tyr Leu Cys Ile Leu
            20                  25                  30

Asp Thr Phe Ser Thr Arg Ala Arg Tyr Leu Phe Leu Leu Ala Gly Gly
        35                  40                  45

Gly Val Leu Ala Phe Ala Ala Met Gly Pro Tyr Ser Leu Leu Ile Phe
    50                  55                  60

Ile Pro Ala Leu Cys Ala Val Ala Leu Val Ser Phe Leu Ser Pro Gln
65                  70                  75                  80

Glu Val His Arg Leu Thr Phe Phe Gln Met Gly Trp Gln Thr Leu
                85                  90                  95

Cys His Leu Gly Leu His Tyr Thr Glu Tyr Tyr Leu Gly Glu Pro Pro
            100                 105                 110

Pro Val Arg Phe Tyr Ile Thr Leu Ser Ser Leu Met Leu Leu Thr Gln
        115                 120                 125

Arg Val Thr Ser Leu Ser Leu Asp Ile Cys Glu Gly Lys Val Glu Ala
    130                 135                 140

Pro Arg Arg Gly Ile Arg Ser Lys Ser Ser Phe Ser Glu His Leu Trp
145                 150                 155                 160

Asp Ala Leu Pro His Phe Ser Tyr Leu Leu Phe Phe Pro Ala Leu Leu
                165                 170                 175

Gly Gly Ser Leu Cys Ser Phe Arg Arg Phe Gln Ala Cys Val Gln Arg
            180                 185                 190

Ser Ser Ser Leu Tyr Pro Ser Ile Ser Phe Arg Ala Leu Thr Trp Arg
        195                 200                 205

Gly Leu Gln Ile Leu Gly Leu Glu Cys Leu Lys Val Ala Leu Arg Ser
    210                 215                 220

Ala Val Ser Ala Gly Ala Gly Leu Asp Asp Cys Gln Arg Leu Glu Cys
225                 230                 235                 240

Ile Tyr Leu Met Trp Ser Thr Ala Trp Leu Phe Lys Leu Thr Tyr Tyr
                245                 250                 255

Ser His Trp Ile Leu Asp Asp Ser Leu Leu His Ala Ala Gly Phe Gly
            260                 265                 270

Ala Glu Ala Gly Gln Gly Pro Gly Glu Glu Gly Tyr Val Pro Asp Val
        275                 280                 285

Asp Ile Trp Thr Leu Glu Thr Thr His Arg Ile Ser Leu Phe Ala Arg
    290                 295                 300

Gln Trp Asn Arg Ser Thr Ala Leu Trp Leu Arg Arg Leu Val Phe Arg
305                 310                 315                 320

Lys Ser Arg Arg Trp Pro Leu Leu Gln Thr Phe Ala Phe Ser Ala Trp
```

|  |  | 325 |  |  |  | 330 |  |  |  | 335 |  |
|--|--|--|--|--|--|--|--|--|--|--|--|
| Trp | His | Gly | Leu | His | Pro | Gly | Gln | Val | Phe | Gly | Phe | Leu | Cys | Trp | Ser |
|  |  |  | 340 |  |  |  |  | 345 |  |  |  |  | 350 |  |  |

Val Met Val Lys Ala Asp Tyr Leu Ile His Thr Phe Ala Asn Val Cys
           355                 360                 365

Ile Arg Ser Trp Pro Leu Arg Leu Leu Tyr Arg Ala Leu Thr Trp Ala
       370                 375                 380

His Thr Gln Leu Ile Ile Ala Tyr Ile Met Leu Ala Val Glu Gly Arg
385                 390                 395                 400

Ser Leu Ser Ser Leu Cys Gln Leu Cys Cys Ser Tyr Asn Ser Leu Phe
               405                 410                 415

Pro Val Met Tyr Gly Leu Leu Leu Phe Leu Leu Ala Glu Arg Lys Asp
           420                 425                 430

Lys Arg Asn
       435

<210> SEQ ID NO 3
<211> LENGTH: 120
<212> TYPE: DNA
<213> ORGANISM: rat

<400> SEQUENCE: 3
atggattggc tccagttctt ctttctccat cctgtatcac tttatcaagg ggctgctttc      60
cccttcgcgc ttctgtttaa ttatctctgc atcacggaat cctttcccac ccgggccagg     120

<210> SEQ ID NO 4
<211> LENGTH: 225
<212> TYPE: DNA
<213> ORGANISM: rat

<400> SEQUENCE: 4
tacctctttc tcctggctgg aggaggtgtc ctggctttgg ccgccatggg tccctacgct      60
ctgctcattt tcatccctgc tctctgtgcc gtggctatga tctcctccct cagtccacag     120
gaagtccatg ggctgacttt cttctttcag atgggttggc aaaccctgtg ccacctgggt     180
cttcactaca aggagtacta cctgtgtgag cctccccctg tgagg                     225

<210> SEQ ID NO 5
<211> LENGTH: 963
<212> TYPE: DNA
<213> ORGANISM: rat

<400> SEQUENCE: 5
ttctacatca ctctttcttc cctcatgctc ttgacgcaga gagtcacgtc tctctccctg      60
gacatttctg aagggaaggt ggaggcagcg tggaggggca ccaggagcag gagttctttg     120
tgtgagcacc tgtgggatgc ctaccctat atcagctatt tgctcttttt ccctgcactc     180
ctgggaggct ccctgtgttc ctttcagaga tttcaggctt gcgttcaaag accaaggtct     240
ttgtatccca gtatctcttt ctgggctctg acctggaggg gtctgcagat ccttgggctg     300
gagtgcctca aggtggcgct gaggagggtg gtgagtgctg gcgctggact ggatgattgc     360
cagcgactgg agtgcatcta catcatgtgg tccaccgctg gctctcttaa actcacctac     420
tactcccact ggatcctgga cgactctctc cttcacgcgg cgggctttgg atctgaggct     480
ggccagaggc ctggagagga gagatacgtc ccggatgtgg acatttggac attggaaact     540
acccacagga tctcccctgtt cgcgaggcag tggaaccgaa gcacagctca gtggctcaag     600

```
aggcttgtct tccagaggag ccggcgctgg cccgtgctgc agactttgc cttctctgcc      660 tggtggcacg gactccaccc aggacaggtg tttggcttcc tgtgctggtc tgtgatggtg      720
aaagccgact atctgatcca cactttgcc aatggatgta tcagatcctg gcccctgcgg      780
ctgctttata gatccctcac ttgggcccac actcagatca tcattgctta cgtaatgctg      840
gccgtggagg ccggagctt ttcctctctc tgccggctgt gctgttctta caacagtatc      900
ttccctgtaa cgtactgcct tttgctttt ctattagcga ggagaaaaca caagtgtaac      960
tga                                                                    963
```

<210> SEQ ID NO 6
<211> LENGTH: 435
<212> TYPE: PRT
<213> ORGANISM: rat

<400> SEQUENCE: 6

```
Met Asp Trp Leu Gln Phe Phe Leu His Pro Val Ser Leu Tyr Gln
 1               5                  10                  15

Gly Ala Ala Phe Pro Phe Ala Leu Leu Phe Asn Tyr Leu Cys Ile Thr
                20                  25                  30

Glu Ser Phe Pro Thr Arg Ala Arg Tyr Leu Phe Leu Leu Ala Gly Gly
            35                  40                  45

Gly Val Leu Ala Leu Ala Ala Met Gly Pro Tyr Ala Leu Leu Ile Phe
        50                  55                  60

Ile Pro Ala Leu Cys Ala Val Ala Met Ile Ser Ser Leu Ser Pro Gln
65                  70                  75                  80

Glu Val His Gly Leu Thr Phe Phe Gln Met Gly Trp Gln Thr Leu
                85                  90                  95

Cys His Leu Gly Leu His Tyr Lys Glu Tyr Tyr Leu Cys Glu Pro Pro
            100                 105                 110

Pro Val Arg Phe Tyr Ile Thr Leu Ser Ser Leu Met Leu Leu Thr Gln
        115                 120                 125

Arg Val Thr Ser Leu Ser Leu Asp Ile Ser Glu Gly Lys Val Glu Ala
    130                 135                 140

Ala Trp Arg Gly Thr Arg Ser Arg Ser Ser Leu Cys Glu His Leu Trp
145                 150                 155                 160

Asp Ala Leu Pro Tyr Ile Ser Tyr Leu Leu Phe Phe Pro Ala Leu Leu
                165                 170                 175

Gly Gly Ser Leu Cys Ser Phe Gln Arg Phe Gln Ala Cys Val Gln Arg
            180                 185                 190

Pro Arg Ser Leu Tyr Pro Ser Ile Ser Phe Trp Ala Leu Thr Trp Arg
        195                 200                 205

Gly Leu Gln Ile Leu Gly Leu Glu Cys Leu Lys Val Ala Leu Arg Arg
    210                 215                 220

Val Val Ser Ala Gly Ala Gly Leu Asp Asp Cys Gln Arg Leu Glu Cys
225                 230                 235                 240

Ile Tyr Ile Met Trp Ser Thr Ala Gly Leu Phe Lys Leu Thr Tyr Tyr
                245                 250                 255

Ser His Trp Ile Leu Asp Asp Ser Leu Leu His Ala Ala Gly Phe Gly
            260                 265                 270

Ser Glu Ala Gly Gln Arg Pro Gly Glu Glu Arg Tyr Val Pro Asp Val
        275                 280                 285

Asp Ile Trp Thr Leu Glu Thr Thr His Arg Ile Ser Leu Phe Ala Arg
    290                 295                 300
```

```
Gln Trp Asn Arg Ser Thr Ala Gln Trp Leu Lys Arg Leu Val Phe Gln
305                 310                 315                 320

Arg Ser Arg Arg Trp Pro Val Leu Gln Thr Phe Ala Phe Ser Ala Trp
            325                 330                 335

Trp His Gly Leu His Pro Gly Gln Val Phe Gly Phe Leu Cys Trp Ser
        340                 345                 350

Val Met Val Lys Ala Asp Tyr Leu Ile His Thr Phe Ala Asn Gly Cys
    355                 360                 365

Ile Arg Ser Trp Pro Leu Arg Leu Leu Tyr Arg Ser Leu Thr Trp Ala
370                 375                 380

His Thr Gln Ile Ile Ile Ala Tyr Val Met Leu Ala Val Glu Gly Arg
385                 390                 395                 400

Ser Phe Ser Ser Leu Cys Arg Leu Cys Cys Ser Tyr Asn Ser Ile Phe
            405                 410                 415

Pro Val Thr Tyr Cys Leu Leu Leu Phe Leu Leu Ala Arg Arg Lys His
            420                 425                 430

Lys Cys Asn
        435

<210> SEQ ID NO 7
<211> LENGTH: 1308
<212> TYPE: DNA
<213> ORGANISM: rat

<400> SEQUENCE: 7
atggattggc tccagttctt ctttctccat cctgtatcac tttatcaagg ggctgctttc      60
cccttcgcgc ttctgtttaa ttatctctgc atcacggaat cctttcccac ccgggccagg     120
tacctctttc tcctggctgg aggaggtgtc ctggctttgg ccgccatggg tccctacgct     180
ctgctcattt tcatccctgc tctctgtgcc gtggctatga tctcctccct cagtccacag     240
gaagtccatg gctgactttt cttctttcag atgggttggc aaaccctgtg ccacctgggt     300
cttcactaca aggagtacta cctgtgtgag cctcccccctg tgaggttcta catcactctt     360
tcttccctca tgtcttgac gcagagagtc acgtctctct ccctggacat ttctgaaggg     420
aaggtggagg cagcgtggag gggcaccagg agcaggagtt ctttgtgtga gcacctgtgg     480
gatgctctac cctatatcag ctatttgctc ttttccctg cactcctggg aggctccctg     540
tgttcctttc agagatttca ggcttgcgtt caaagaccaa ggtctttgta tcccagtatc     600
tctttctggg ctctgacctg gaggggtctg cagatccttg gctggagtg cctcaaggtg     660 gcgctgagga gggtggtgag tgctggcgct ggactggatg attgccagcg actggagtgc     720
atctacatca tgtggtccac cgctgggctc tttaaaactca cctactactc ccactggatc     780
ctggacgact ctctccttca cgcggcgggc tttggatctg aggctggcca gaggcctgga     840
gaggagagat acgtcccgga tgtggacatt tggacattgg aaactaccca caggatctcc     900
ctgttcgcga ggcagtggaa ccgaagcaca gctcagtggc tcaagaggct tgtcttccag     960
aggagccggc gctggcccgt gctgcagact tttgccttct ctgcctggtg gcacggactc    1020
cacccaggac aggtgtttgg cttcctgtgc tggtctgtga tggtgaaagc cgactatctg    1080
atccacactt tgccaatgg atgtatcaga tcctggcccc tgcggctgct ttatagatcc    1140
ctcacttggg cccacactca gatcatcatt gcttacgtaa tgctggccgt ggagggccgg    1200 agctttcct ctctctgccg gctgtgctgt tcttacaaca gtatcttccc tgtaacgtac    1260
tgccttttgc ttttctatt agcgaggaga aaacacaagt gtaactga                 1308
```

<210> SEQ ID NO 8
<211> LENGTH: 120
<212> TYPE: DNA
<213> ORGANISM: human

<400> SEQUENCE: 8

```
atggagtggc tttggctgtt ctttctccat cctatatcgt tttaccaggg ggctgcattt      60
ccctttgcac ttctcttcaa ttatctctgc atcatggatt cattctccac tcgtgccagg     120
```

<210> SEQ ID NO 9
<211> LENGTH: 225
<212> TYPE: DNA
<213> ORGANISM: human

<400> SEQUENCE: 9

```
tacctctttc tcctgactgg aggaggtgcc ctggccgtgg ctgccatggg ttcctacgcc      60
gtgctcgtct tcaccctgc tgtctgcgct gtggctctcc tctgttccct ggctcctcag     120
caagtccaca ggtggacctt ctgctttcag atgagctggc agaccttgtg tcacctaggt     180
ctgcactaca ctgagtatta tctgcatgag cctccttctg tgagg                    225
```

<210> SEQ ID NO 10
<211> LENGTH: 963
<212> TYPE: DNA
<213> ORGANISM: human

<400> SEQUENCE: 10

```
ttctgcatca ctctttcttc tctcatgctc ttgacccaga gggtcacgtc cctctctctg      60
gacatttgtg aggggaaagt gaaggcagca tctggaggct tcaggagcag gagctctttg     120
tctgagcatg tgtgtaaggc actgccctat tcagctact tgctcttttt ccctgctctc     180
ctgggaggct ctctgtgctc cttccagcga tttcaggctc gtgttcaagg gtccagtgct    240
ttgcatccca gacactcttt ctgggctctg agctggaggg gtctgcagat tcttggacta    300
gaatgcctaa acgtggcagt gagcagggtg gtggatgcag gagcgggact gactgattgc    360
cagcaattcg agtgcatcta tgtcgtgtgg accacagctg ggcttttcaa gctcacctac    420
tactcccact ggatcctgga cgactccctc ctccacgcag cgggctttgg gcctgagctt    480
ggtcagagcc ctggagagga gggatatgtc cccgatgcag acatctggac cctggaaaga    540
acccacagga tatctgtgtt ctcaagaaag tggaaccaaa gcacagctcg atggctccga    600
cggcttgtat tccagcacag cagggcttgg ccgttgttgc agacatttgc cttctctgcc    660
tggtggcatg gactccatcc aggacaggtg tttggtttcg tttgctgggc cgtgatggtg    720
gaagctgact acctgattca ctcctttgcc aatgagttta tcagatcctg gccgatgagg    780
ctgttctata gaaccctcac ctgggcccac acccagttga tcattgccta catcatgctg    840
gctgtggagt caggagtctc tcctctctc tggttgctct gtaattcgta caacagtgtc    900
tttcccatgg tgtactgtat tctgcttttg ctattggcga agagaaagca caaatgtaac    960
tga                                                                   963
```

<210> SEQ ID NO 11
<211> LENGTH: 435
<212> TYPE: PRT
<213> ORGANISM: human

<400> SEQUENCE: 11

Met Glu Trp Leu Trp Leu Phe Phe Leu His Pro Ile Ser Phe Tyr Gln

-continued

```
1               5                   10                  15
Gly Ala Ala Phe Pro Phe Ala Leu Leu Phe Asn Tyr Leu Cys Ile Met
                20                  25                  30

Asp Ser Phe Ser Thr Arg Ala Arg Tyr Leu Phe Leu Leu Thr Gly Gly
            35                  40                  45

Gly Ala Leu Ala Val Ala Ala Met Gly Ser Tyr Ala Val Leu Val Phe
            50                  55                  60

Thr Pro Ala Val Cys Ala Val Ala Leu Leu Cys Ser Leu Ala Pro Gln
65                  70                  75                  80

Gln Val His Arg Trp Thr Phe Cys Phe Gln Met Ser Trp Gln Thr Leu
                85                  90                  95

Cys His Leu Gly Leu His Tyr Thr Glu Tyr Tyr Leu His Glu Pro Pro
                100                 105                 110

Ser Val Arg Phe Cys Ile Thr Leu Ser Ser Leu Met Leu Leu Thr Gln
            115                 120                 125

Arg Val Thr Ser Leu Ser Leu Asp Ile Cys Glu Gly Lys Val Lys Ala
            130                 135                 140

Ala Ser Gly Gly Phe Arg Ser Arg Ser Ser Leu Ser Glu His Val Cys
145                 150                 155                 160

Lys Ala Leu Pro Tyr Phe Ser Tyr Leu Leu Phe Phe Pro Ala Leu Leu
                165                 170                 175

Gly Gly Ser Leu Cys Ser Phe Gln Arg Phe Gln Ala Arg Val Gln Gly
                180                 185                 190

Ser Ser Ala Leu His Pro Arg His Ser Phe Trp Ala Leu Ser Trp Arg
            195                 200                 205

Gly Leu Gln Ile Leu Gly Leu Glu Cys Leu Asn Val Ala Val Ser Arg
            210                 215                 220

Val Val Asp Ala Gly Ala Gly Leu Thr Asp Cys Gln Gln Phe Glu Cys
225                 230                 235                 240

Ile Tyr Val Val Trp Thr Thr Ala Gly Leu Phe Lys Leu Thr Tyr Tyr
                245                 250                 255

Ser His Trp Ile Leu Asp Asp Ser Leu Leu His Ala Ala Gly Phe Gly
                260                 265                 270

Pro Glu Leu Gly Gln Ser Pro Gly Glu Glu Gly Tyr Val Pro Asp Ala
            275                 280                 285

Asp Ile Trp Thr Leu Glu Arg Thr His Arg Ile Ser Val Phe Ser Arg
            290                 295                 300

Lys Trp Asn Gln Ser Thr Ala Arg Trp Leu Arg Arg Leu Val Phe Gln
305                 310                 315                 320

His Ser Arg Ala Trp Pro Leu Leu Gln Thr Phe Ala Phe Ser Ala Trp
            325                 330                 335

Trp His Gly Leu His Pro Gly Gln Val Phe Gly Phe Val Cys Trp Ala
            340                 345                 350

Val Met Val Glu Ala Asp Tyr Leu Ile His Ser Phe Ala Asn Glu Phe
            355                 360                 365

Ile Arg Ser Trp Pro Met Arg Leu Phe Tyr Arg Thr Leu Thr Trp Ala
            370                 375                 380

His Thr Gln Leu Ile Ile Ala Tyr Ile Met Leu Ala Val Glu Val Arg
385                 390                 395                 400

Ser Leu Ser Ser Leu Trp Leu Leu Cys Asn Ser Tyr Asn Ser Val Phe
                405                 410                 415

Pro Met Val Tyr Cys Ile Leu Leu Leu Leu Ala Lys Arg Lys His
                420                 425                 430
```

Lys Cys Asn
      435

<210> SEQ ID NO 12
<211> LENGTH: 1308
<212> TYPE: DNA
<213> ORGANISM: human

<400> SEQUENCE: 12

```
atggagtggc tttggctgtt ctttctccat cctatatcgt tttaccaggg ggctgcattt     60
cccttttgcac ttctcttcaa ttatctctgc atcatggatt cattctccac tcgtgccagg    120
tacctctttc tcctgactgg aggaggtgcc ctggccgtgg ctgccatggg ttcctacgcc    180
gtgctcgtct tcaccctgc tgtctgcgct gtggctctcc tctgttccct ggctcctcag    240
caagtccaca ggtggacctt ctgctttcag atgagctggc agaccttgtg tcacctaggt    300
ctgcactaca ctgagtatta tctgcatgag cctccttctg tgaggttctg catcactctt    360
tcttctctca tgctcttgac ccagagggtc acgtccctct ctctggacat tgtgagggg    420
aaagtgaagg cagcatctgg aggcttcagg agcaggagct ctttgtctga gcatgtgtgt    480
aaggcactgc cctatttcag ctacttgctc ttttttccctg ctctcctggg aggctctctg    540
tgctccttcc agcgatttca ggctcgtgtt caagggtcca gtgctttgca tcccagacac    600
tctttctggg ctctgagctg gagggtctg cagattcttg gactagaatg cctaaacgtg    660
gcagtgagca gggtggtgga tgcaggagcg ggactgactg attgccagca attcgagtgc    720
atctatgtcg tgtggaccac agctgggctt ttcaagctca cctactactc ccactggatc    780
ctggacgact ccctcctcca cgcagcgggc tttgggcctg agcttggtca gagccctgga    840
gaggagggat atgtccccga tgcagacatc tggaccctgg aaagaaccca caggatatct    900
gtgttctcaa gaaagtggaa ccaaagcaca gctcgatggc tccgacggct tgtattccag    960
cacagcaggg cttggccgtt gttgcagaca tttgccttct ctgcctggtg gcatggactc   1020
catccaggac aggtgtttgg tttcgtttgc tgggccgtga tggtggaagc tgactacctg   1080
attcactcct tgccaatga gtttatcaga tcctggccga tgaggctgtt ctatagaacc   1140
ctcacctggg cccacaccca gttgatcatt gcctacatca tgctggctgt ggaggtcagg   1200
agtctctcct ctctctggtt gctctgtaat tcgtacaaca gtgtctttcc catggtgtac   1260
tgtattctgc ttttgctatt ggcgaagaga aagcacaaat gtaactga                1308
```

<210> SEQ ID NO 13
<211> LENGTH: 435
<212> TYPE: PRT
<213> ORGANISM: chimpanzee

<400> SEQUENCE: 13

Met Glu Trp Leu Arg Leu Phe Phe Leu His Pro Val Ser Phe Tyr Gln
1               5                   10                  15

Gly Ala Ala Phe Pro Phe Ala Leu Leu Phe Asn Tyr Leu Cys Ile Met
            20                  25                  30

Asp Ser Phe Ser Thr Arg Ala Arg Tyr Leu Phe Leu Leu Ala Gly Gly
        35                  40                  45

Gly Ala Leu Ala Val Ala Ala Met Gly Ser Tyr Ala Val Leu Val Phe
    50                  55                  60

Thr Pro Ala Val Cys Ala Val Ala Leu Leu Cys Ser Leu Ala Pro Gln
65                  70                  75                  80

```
Gln Val His Arg Trp Thr Phe Cys Phe Gln Met Ser Trp Gln Thr Leu
                85                  90                  95

Cys His Leu Gly Leu His Tyr Thr Glu Tyr Tyr Leu His Glu Pro Pro
            100                 105                 110

Ser Val Arg Phe Cys Ile Thr Leu Ser Ser Leu Met Leu Leu Thr Gln
            115                 120                 125

Arg Val Thr Ser Leu Ser Leu Asp Ile Cys Glu Gly Lys Val Glu Ala
        130                 135                 140

Ala Ser Gly Gly Phe Arg Ser Arg Ser Ser Leu Ser Glu His Val Cys
145                 150                 155                 160

Lys Ala Leu Pro Tyr Phe Ser Tyr Leu Leu Phe Phe Pro Ala Leu Leu
                165                 170                 175

Gly Gly Ser Leu Cys Ser Phe Gln Arg Phe Gln Ala Arg Val Gln Gly
            180                 185                 190

Ser Ser Ala Leu His Pro Arg His Ser Phe Trp Ala Leu Ser Trp Arg
        195                 200                 205

Cys Leu Gln Ile Leu Gly Leu Glu Cys Leu Asn Val Ala Val Ser Arg
210                 215                 220

Val Val Asp Ala Gly Ala Gly Leu Thr Asp Cys Gln Gln Phe Glu Cys
225                 230                 235                 240

Ile Tyr Val Val Trp Thr Thr Ala Gly Leu Phe Lys Leu Thr Tyr Tyr
                245                 250                 255

Ser His Trp Ile Leu Asp Asp Ser Leu Leu His Ala Ala Gly Phe Gly
            260                 265                 270

Pro Glu Leu Gly Gln Ser Pro Gly Glu Gly Tyr Val Pro Asp Ala
        275                 280                 285

Asp Ile Trp Thr Leu Glu Arg Thr His Arg Ile Ser Val Phe Ala Arg
        290                 295                 300

Lys Trp Asn Gln Ser Thr Ala Arg Trp Leu Arg Arg Leu Val Phe Gln
305                 310                 315                 320

His Ser Arg Ala Trp Pro Leu Leu Gln Thr Phe Ala Phe Ser Ala Trp
                325                 330                 335

Trp His Gly Leu His Pro Gly Gln Val Phe Gly Phe Val Cys Trp Ala
            340                 345                 350

Val Met Val Glu Ala Asp Tyr Leu Ile His Ser Phe Ala Asn Glu Phe
        355                 360                 365

Ile Arg Ser Trp Pro Met Arg Leu Phe Tyr Arg Thr Leu Thr Trp Ala
        370                 375                 380

His Thr Gln Leu Ile Ile Ala Tyr Ile Met Leu Ala Val Glu Val Arg
385                 390                 395                 400

Ser Leu Ser Leu Trp Leu Leu Cys Asn Ser Tyr Asn Ser Val Phe
                405                 410                 415

Pro Met Val Tyr Cys Ile Leu Leu Leu Leu Val Lys Arg Lys His
            420                 425                 430

Lys Cys Asn
        435

<210> SEQ ID NO 14
<211> LENGTH: 120
<212> TYPE: DNA
<213> ORGANISM: bovine

<400> SEQUENCE: 14
atggattggc tccagctgtt cttccttgat cctgtatcac tttatcaagg agctgctttt    60
```

```
cctttttgcac ttctgtttaa tcatctctgt gttatggatt cattttccac tcaggccagg    120
```

<210> SEQ ID NO 15
<211> LENGTH: 225
<212> TYPE: DNA
<213> ORGANISM: bovine

<400> SEQUENCE: 15

```
tacctgttcc tcctggcggg aggcggtgcc ctggccgtgg ctgctatggg tgccttcgct    60
gtgctggtct tcatccccgc cctgtgcacg gtggtcctca tccactcgct tggcccccag    120
gatgtccaca ggccgacctt cctctttcag atgacctggc agacgctgtg ccacctgggt    180
ctgcactata cggagtatta tctgcaagaa gctccttcta caagg                   225
```

<210> SEQ ID NO 16
<211> LENGTH: 963
<212> TYPE: DNA
<213> ORGANISM: bovine

<400> SEQUENCE: 16

```
ttctgcatca ctctctcttc gctcatgctc ttgacccaga agatcacatc tctgtctctg    60
gatattcgtg agggggaaggt ggtagcacca tcaggacgca tccctaacaa gaattctttg   120
tctgagcatc tgcatgcggc tcttccctat ctcagctact tgctcttctt ccctgccctc    180
ctaggaggcc cgctgtgttc cttccagagg tttcaggctc gagttgaagg gtccagcagt    240
ttgtggtcca ggcactcttt ctgggctctg acctggaggg cgctgcagat cctgggactg    300
gagagtctga aggtgatcgt cagcggggtg gtgggcgtgg gggcaggact tggaggctgc    360
aggcagctgc agtgcgtctt cgtcctgtgg tccacggccg ggctcttcaa actcacctac    420
tactcccact ggctcctgga tgacgccctc ctccgcgcgg ccggctttgg atctgagtta    480
ggtcgcagcc cgggtgagga gggactcctc cccgatgcgg acatttggac gctggaaacg    540
acccacagga tagccctgtt cgccaggaag tggaaccaga gcacggctcg gtggctccga    600
cgcctggttt tccagcagcg caggacctgg cccttgttgc agacattcct cttctcggcc    660
tggtggcacg gtctccaccc gggacaggtg tttggtttcc tctgctgggc tgtcatggtg    720
gaagccgact acctgattca cgccttcgcc agcgtgttca tcagctcctg gcccatgcgg    780
ctgctctaca gagccctggc ctgggcccac acccagctca tcatcgccta cataatgctg    840
gccgtggagg cccggagcct ctcctctctc tggctgctgt ggaattctta cagcagtgtc    900
tttcccacgg tgtactgtat tttgcttctc ctgttagcaa agagaaagca taaatgcaac    960
tga                                                                 963
```

<210> SEQ ID NO 17
<211> LENGTH: 435
<212> TYPE: PRT
<213> ORGANISM: bovine

<400> SEQUENCE: 17

```
Met Asp Trp Leu Gln Leu Phe Phe Leu Asp Pro Val Ser Leu Tyr Gln
1               5                   10                  15

Gly Ala Ala Phe Pro Phe Ala Leu Leu Phe Asn His Leu Cys Val Met
            20                  25                  30

Asp Ser Phe Ser Thr Gln Ala Arg Tyr Leu Phe Leu Leu Ala Gly Gly
        35                  40                  45

Gly Ala Leu Ala Val Ala Ala Met Gly Ala Phe Ala Val Leu Val Phe
    50                  55                  60
```

Ile Pro Ala Leu Cys Thr Val Val Leu Ile His Ser Leu Gly Pro Gln
65                  70                  75                  80

Asp Val His Arg Pro Thr Phe Leu Phe Gln Met Thr Trp Gln Thr Leu
                85                  90                  95

Cys His Leu Gly Leu His Tyr Thr Glu Tyr Tyr Leu Gln Glu Ala Pro
            100                 105                 110

Ser Thr Arg Phe Cys Ile Thr Leu Ser Ser Leu Met Leu Leu Thr Gln
        115                 120                 125

Lys Ile Thr Ser Leu Ser Leu Asp Ile Arg Glu Gly Lys Val Val Ala
130                 135                 140

Pro Ser Gly Arg Ile Pro Asn Lys Asn Ser Leu Ser Glu His Leu His
145                 150                 155                 160

Ala Ala Leu Pro Tyr Leu Ser Tyr Leu Leu Phe Phe Pro Ala Leu Leu
                165                 170                 175

Gly Gly Pro Leu Cys Ser Phe Gln Arg Phe Gln Ala Arg Val Glu Gly
            180                 185                 190

Ser Ser Ser Leu Trp Ser Arg His Ser Phe Trp Ala Leu Thr Trp Arg
        195                 200                 205

Ala Leu Gln Ile Leu Gly Leu Glu Ser Leu Lys Val Ile Val Ser Gly
210                 215                 220

Val Val Gly Val Gly Ala Gly Leu Gly Gly Cys Arg Gln Leu Gln Cys
225                 230                 235                 240

Val Phe Val Leu Trp Ser Thr Ala Gly Leu Phe Lys Leu Thr Tyr Tyr
                245                 250                 255

Ser His Trp Leu Leu Asp Asp Ala Leu Leu Arg Ala Ala Gly Phe Gly
            260                 265                 270

Ser Glu Leu Gly Arg Ser Pro Gly Glu Gly Leu Leu Pro Asp Ala
        275                 280                 285

Asp Ile Trp Thr Leu Glu Thr Thr His Arg Ile Ala Leu Phe Ala Arg
290                 295                 300

Lys Trp Asn Gln Ser Thr Ala Arg Trp Leu Arg Arg Leu Val Phe Gln
305                 310                 315                 320

Gln Arg Arg Thr Trp Pro Leu Leu Gln Thr Phe Leu Phe Ser Ala Trp
                325                 330                 335

Trp His Gly Leu His Pro Gly Gln Val Phe Gly Phe Leu Cys Trp Ala
            340                 345                 350

Val Met Val Glu Ala Asp Tyr Leu Ile His Ala Phe Ala Ser Val Phe
        355                 360                 365

Ile Ser Ser Trp Pro Met Arg Leu Leu Tyr Arg Ala Leu Ala Trp Ala
370                 375                 380

His Thr Gln Leu Ile Ile Ala Tyr Ile Met Leu Ala Val Glu Ala Arg
385                 390                 395                 400

Ser Leu Ser Ser Leu Trp Leu Leu Trp Asn Ser Tyr Ser Ser Val Phe
                405                 410                 415

Pro Thr Val Tyr Cys Ile Leu Leu Leu Leu Ala Lys Arg Lys His
            420                 425                 430

Lys Cys Asn
        435

<210> SEQ ID NO 18
<211> LENGTH: 1308
<212> TYPE: DNA
<213> ORGANISM: bovine

<400> SEQUENCE: 18

```
atggattggc tccagctgtt cttccttgat cctgtatcac tttatcaagg agctgctttt      60
ccttttgcac ttctgtttaa tcatctctgt gttatggatt cattttccac tcaggccagg    120
tacctgttcc tcctggcggg aggcggtgcc ctggccgtgg ctgctatggg tgccttcgct    180
gtgctggtct tcatcccgc cctgtgcacg gtggtcctca tccactcgct tggccccag     240
gatgtccaca ggccgacctt cctctttcag atgacctggc agacgctgtg ccacctgggt    300
ctgcactata cggagtatta tctgcaagaa gctccttcta caaggttctg catcactctc    360
tcttcgctca tgctcttgac ccagaagatc acatctctgt ctctggatat tcgtgagggg    420
aaggtggtag caccatcagg acgcatccct aacaagaatt ctttgtctga gcatctgcat    480
gcggctcttc cctatctcag ctacttgctc ttcttccctg ccctcctagg aggcccgctg    540
tgttccttcc agaggtttca ggctcgagtt gaagggtcca gcagtttgtg gtccaggcac    600
tctttctggg ctctgacctg gagggcgctg cagatcctgg gactggagag tctgaaggtg    660
atcgtcagcg gggtggtggg cgtgggggca ggacttggag gctgcaggca gctgcagtgc    720
gtcttcgtcc tgtggtccac ggccgggctc ttcaaactca cctactactc ccactggctc    780
ctggatgacg ccctcctccg cgcggccggc tttggatctg agttaggtcg cagcccgggt    840
gaggagggac tcctccccga tgcggacatt tggacgctgg aaacgaccca caggatagcc    900
ctgttcgcca ggaagtggaa ccagagcacg gctcggtggc tccgacgcct ggttttccag    960
cagcgcagga cctggccctt gttgcagaca ttcctcttct cggcctggtg gcacggtctc   1020
caccgggac aggtgtttgg tttcctctgc tgggctgtca tggtggaagc cgactacctg   1080
attcacgcct cgccagcgt gttcatcagc tcctggccca tgcggctgct ctacagagcc   1140
ctggcctggg cccacaccca gctcatcatc gcctacataa tgctggccgt ggaggcccgg   1200
agcctctcct ctctctggct gctgtggaat tcttacagca gtgtctttcc cacggtgtac   1260
tgtattttgc ttctcctgtt agcaaagaga aagcataaat gcaactga               1308
```

<210> SEQ ID NO 19
<211> LENGTH: 120
<212> TYPE: DNA
<213> ORGANISM: horse

<400> SEQUENCE: 19

```
atgggttggc ttcagctgtt ccttctccat cctgtatcac tttatcaagg ggccgctttt      60
ccttttgcac ttctatttaa ttacctttgc actatggatt cattttccac tcatgccagg    120
```

<210> SEQ ID NO 20
<211> LENGTH: 225
<212> TYPE: DNA
<213> ORGANISM: horse

<400> SEQUENCE: 20

```
tacctctttc tgctggcagg aggaggcgcc ctggccttgg ccgctatggg tcccttgct      60
gtgcttgtct tcatccctgc gatatgtgct gtgtttctga tctgcttgct cagcccacag    120
gaagtccaca ggcagacttt ctgctttcag atgagctggc agacgctgtg tcacctgggt    180
ctgcactata ctgagtatta tctgcaagaa cttccttcca cgagg                    225
```

<210> SEQ ID NO 21
<211> LENGTH: 963
<212> TYPE: DNA
<213> ORGANISM: horse

<400> SEQUENCE: 21

```
ttctgcctcg ctctttcttc cctcatgctc ttgacccaga gggtcacatc cctctctctg      60
gacatttgtg aagggaaact ggcagcagca tcaggaggca ccaggagcag aagctctttg     120
tctgagcatc tgtgtaaggc actgccctat ttcagctact tgcttttttt tcctgctctc     180
ctaggaggcc ctctgtgttc cttccagaga tttcaggccc gtgttcaagg cccagcaac     240
ttgtgtccca ggcaccctt cagggctctg acctggaggg gtctgcagat tctgggacta     300
gagtgcctaa aggtcgtcat gagggcagtg gtgagagcag gagcaggact gaccgactgc     360
cggcaactcc agtgcatcta tgtcatgtgg tccacagccg ggctcttcaa actcacctac     420
tactcccact ggatcctgga tgactccctc tgtgtgcag cgggctttgg atctgagttt     480
gggcagagcc ctggtgagga cggatacatc cctgatgcag acatttggac actggaaaca     540
acccacagga tatccctgtt tgcgagaaag tggaaccaaa gcacagctcg gtggctcaga     600
cgcctcgtat ttcagcacag cagggtctgg ccgttgttgc agacatttgc attctctgcc     660
tggtggcatg ggctccatcc aggacaggtg tttggtttcc tctgctgggc tgtgatggtg     720
gaagctgact acctgattca cacctttgcc aaattgttta tcagatcctg gccgatgaag     780
ctgctctata gaactctgac ctgggcccac acccagctca tcattgccta cataatgctg     840
gccgtggagg tcaggagcct ctcctctctc tggctgctgt gtaattctta caacagtgtc     900
tttcccatgg tgtattgtat tttgcttttg ctattagcaa agagaaagca cacatttaac     960
tga                                                                    963
```

<210> SEQ ID NO 22
<211> LENGTH: 435
<212> TYPE: PRT
<213> ORGANISM: horse

<400> SEQUENCE: 22

```
Met Gly Trp Leu Gln Leu Phe Leu Leu His Pro Val Ser Leu Tyr Gln
1               5                   10                  15

Gly Ala Ala Phe Pro Phe Ala Leu Leu Phe Asn Tyr Leu Cys Thr Met
            20                  25                  30

Asp Ser Phe Ser Thr His Ala Arg Tyr Leu Phe Leu Leu Ala Gly Gly
        35                  40                  45

Gly Ala Leu Ala Leu Ala Ala Met Gly Pro Phe Ala Val Leu Val Phe
    50                  55                  60

Ile Pro Ala Ile Cys Ala Val Phe Leu Ile Cys Leu Leu Ser Pro Gln
65                  70                  75                  80

Glu Val His Arg Gln Thr Phe Cys Phe Gln Met Ser Trp Gln Thr Leu
                85                  90                  95

Cys His Leu Gly Leu His Tyr Thr Glu Tyr Tyr Leu Gln Glu Leu Pro
            100                 105                 110

Ser Thr Arg Phe Cys Leu Ala Leu Ser Ser Leu Met Leu Leu Thr Gln
        115                 120                 125

Arg Val Thr Ser Leu Ser Leu Asp Ile Cys Glu Gly Lys Leu Ala Ala
    130                 135                 140

Ala Ser Gly Gly Thr Arg Ser Arg Ser Ser Leu Ser Glu His Leu Cys
145                 150                 155                 160

Lys Ala Leu Pro Tyr Phe Ser Tyr Leu Leu Phe Phe Pro Ala Leu Leu
                165                 170                 175

Gly Gly Pro Leu Cys Ser Phe Gln Arg Phe Gln Ala Arg Val Gln Gly
```

```
                     180                 185                 190
Pro Ser Asn Leu Cys Pro Arg His Pro Phe Arg Ala Leu Thr Trp Arg
            195                 200                 205
Gly Leu Gln Ile Leu Gly Leu Glu Cys Leu Lys Val Val Met Arg Ala
        210                 215                 220
Val Val Arg Ala Gly Ala Gly Leu Thr Asp Cys Arg Gln Leu Gln Cys
225                 230                 235                 240
Ile Tyr Val Met Trp Ser Thr Ala Gly Leu Phe Lys Leu Thr Tyr Tyr
                245                 250                 255
Ser His Trp Ile Leu Asp Asp Ser Leu Leu Cys Ala Ala Gly Phe Gly
            260                 265                 270
Ser Glu Phe Gly Gln Ser Pro Gly Glu Asp Gly Tyr Ile Pro Asp Ala
        275                 280                 285
Asp Ile Trp Thr Leu Glu Thr Thr His Arg Ile Ser Leu Phe Ala Arg
    290                 295                 300
Lys Trp Asn Gln Ser Thr Ala Arg Trp Leu Arg Arg Leu Val Phe Gln
305                 310                 315                 320
His Ser Arg Val Trp Pro Leu Leu Gln Thr Phe Ala Phe Ser Ala Trp
                325                 330                 335
Trp His Gly Leu His Pro Gly Gln Val Phe Gly Phe Leu Cys Trp Ala
            340                 345                 350
Val Met Val Glu Ala Asp Tyr Leu Ile His Thr Phe Ala Lys Leu Phe
        355                 360                 365
Ile Arg Ser Trp Pro Met Lys Leu Leu Tyr Arg Thr Leu Thr Trp Ala
    370                 375                 380
His Thr Gln Leu Ile Ile Ala Tyr Ile Met Leu Ala Val Glu Val Arg
385                 390                 395                 400
Ser Leu Ser Ser Leu Trp Leu Leu Cys Asn Ser Tyr Asn Ser Val Phe
                405                 410                 415
Pro Met Val Tyr Cys Ile Leu Leu Leu Leu Ala Lys Arg Lys His
            420                 425                 430
Thr Phe Asn
        435

<210> SEQ ID NO 23
<211> LENGTH: 1308
<212> TYPE: DNA
<213> ORGANISM: horse

<400> SEQUENCE: 23
atgggttggc ttcagctgtt ccttctccat cctgtatcac tttatcaagg ggccgctttt       60
ccttttgcac ttctatttaa ttacctttgc actatggatt cattttccac tcatgccagg      120
tacctctttc tgctggcagg aggaggcgcc ctggccttgg ccgctatggg tcccttcgct      180
gtgcttgtct tcatccctgc gatatgtgct gtgtttctga tctgcttgct cagcccacag      240
gaagtccaca ggcagacttt ctgctttcag atgagctggc agacgctgtg tcacctgggt      300
ctgcactata ctgagtatta tctgcaagaa cttccttcca cgaggttctg cctcgctctt      360
tcttccctca tgctcttgac ccagagggtc acatccctct ctctggacat tgtgaaggg       420 aaactggcag cagcatcagg aggcaccagg agcagaagct ctttgtctga gcatctgtgt      480
aaggcactgc cctatttcag ctacttgctt tttttttcctg ctctcctagg aggccctctg     540
tgttccttcc agagatttca ggcccgtgtt caagggccca gcaacttgtg tcccaggcac      600
```

-continued

```
cctttcaggg ctctgacctg gagggtctg cagattctgg gactagagtg cctaaaggtc      660
gtcatgaggg cagtggtgag agcaggagca ggactgaccg actgccggca actccagtgc      720
atctatgtca tgtggtccac agccgggctc ttcaaactca cctactactc ccactggatc      780
ctggatgact ccctcctgtg tgcagcgggc tttggatctg agtttgggca gagccctggt      840
gaggacggat acatccctga tgcagacatt tggacactgg aaacaaccca caggatatcc      900
ctgtttgcga gaaagtggaa ccaaagcaca gctcggtggc tcagacgcct cgtatttcag      960
cacagcaggg tctggccgtt gttgcagaca tttgcattct ctgcctggtg catgggctc     1020 catccaggac aggtgtttgg tttcctctgc tgggctgtga tggtggaagc tgactacctg    1080
attcacacct ttgccaaatt gtttatcaga tcctggccga tgaagctgct ctatagaact     1140
ctgacctggg cccacaccca gctcatcatt gcctacataa tgctggccgt ggaggtcagg    1200
agcctctcct ctctctggct gctgtgtaat tcttacaaca gtgtctttcc catggtgtat    1260
tgtattttgc ttttgctatt agcaaagaga aagcacacat ttaactga                 1308

<210> SEQ ID NO 24
<211> LENGTH: 126
<212> TYPE: DNA
<213> ORGANISM: zebrafish

<400> SEQUENCE: 24
atgatagatc tcctttggat ttcttctgat ggacaccctc agctgtttta ccagtttatc       60
aacataccat ttgcatttct gtttcattgc ttatccagtc aaggacatct ctcgataatc      120
aacagg                                                                 126

<210> SEQ ID NO 25
<211> LENGTH: 225
<212> TYPE: DNA
<213> ORGANISM: zebrafish

<400> SEQUENCE: 25
tacgtctatt tggcgatggg aggattcatg ctggctattg caacaatggg tccatatagc       60
tcactgctgt tcctgagtgc tattaaactg ctgttactga tccactatat acatccaatg      120
catcttcatc ggtggattct gggactgcag atgtgttggc aaacctgctg gcatttgtac      180
gtccagtacc agatatactg gcttcaagag gcaccagact caagg                      225

<210> SEQ ID NO 26
<211> LENGTH: 897
<212> TYPE: DNA
<213> ORGANISM: zebrafish

<400> SEQUENCE: 26
cttttactgg ccatatctgc actcatgttg atgacccaga ggatttcctc tctatcactc       60
gatttccaag aggggacgat ctccaatcag tcaatcctta ttccattcct aacctactcg      120
ctttatttcc ctgcccttct tggaggtcca ctttgcagtt tcaatgcttt tgttcagtct     180
gtcgagcgtc aacacaccag catgacttca tatttaggaa atctcacttc aaagatatca      240
caagttatag ttttggtgtg gattaaacag cttttcagtg agcttttgaa atctgccacg      300
tttaacatcg acagtgtttg tcttgatgta ttgtggattt ggatcttttc gctgacactt      360
aggcttaatt actatgcaca ctggaagatg agcgagtgtg ttaataatgc tgcaggattt      420
```

```
ggtgtctatt tacacaaaca cagtggacaa acatcatggg acggtctttc tgatgggagt    480
gtactggtga ctgaagcatc cagtcgtcct tcggttttg cgcgaaagtg gaaccaaacc    540
acggtggatt ggcttcgaaa aatagtcttc aacaggacca gcagatctcc actgttcatg    600
acttttgggt tttctgcact gtggcacggt cttcaccctg gcagattct gggtttcctc     660 atttgggccg tcactgtgca ggcggactac aaactgcatc gcttcttgca cccgaagctt    720
aactccctgt ggagaaaacg gctgtatgtg tgtgtaaact gggcctttac tcagctgacc    780
gtcgcatgtg ttgtggtctg tgtggagctt cagagtttgg catcagttaa gctgctctgg    840
tcttcgtgta ttgctgtgtt tccactgctg agtgctctga tcttaataat cctctga       897
```

<210> SEQ ID NO 27  
<211> LENGTH: 415  
<212> TYPE: PRT  
<213> ORGANISM: zebrafish
<400> SEQUENCE: 27

```
Met Ile Asp Leu Leu Trp Ile Ser Ser Asp Gly His Pro Gln Leu Phe
1               5                   10                  15

Tyr Gln Phe Ile Asn Ile Pro Phe Ala Phe Leu Phe His Cys Leu Ser
            20                  25                  30

Ser Gln Gly His Leu Ser Ile Ile Asn Arg Tyr Val Tyr Leu Ala Met
        35                  40                  45

Gly Gly Phe Met Leu Ala Ile Ala Thr Met Gly Pro Tyr Ser Ser Leu
    50                  55                  60

Leu Phe Leu Ser Ala Ile Lys Leu Leu Leu Ile His Tyr Ile His
65                  70                  75                  80

Pro Met His Leu His Arg Trp Ile Leu Gly Leu Gln Met Cys Trp Gln
                85                  90                  95

Thr Cys Trp His Leu Tyr Val Gln Tyr Gln Ile Tyr Trp Leu Gln Glu
            100                 105                 110

Ala Pro Asp Ser Arg Leu Leu Leu Ala Ile Ser Ala Leu Met Leu Met
        115                 120                 125

Thr Gln Arg Ile Ser Ser Leu Ser Leu Asp Phe Gln Glu Gly Thr Ile
    130                 135                 140

Ser Asn Gln Ser Ile Leu Ile Pro Phe Leu Thr Tyr Ser Leu Tyr Phe
145                 150                 155                 160

Pro Ala Leu Leu Gly Gly Pro Leu Cys Ser Phe Asn Ala Phe Val Gln
                165                 170                 175

Ser Val Glu Arg Gln His Thr Ser Met Thr Ser Tyr Leu Gly Asn Leu
            180                 185                 190

Thr Ser Lys Ile Ser Gln Val Ile Val Leu Val Trp Ile Lys Gln Leu
        195                 200                 205

Phe Ser Glu Leu Leu Lys Ser Ala Thr Phe Asn Ile Asp Ser Val Cys
    210                 215                 220

Leu Asp Val Leu Trp Ile Trp Ile Phe Ser Leu Thr Leu Arg Leu Asn
225                 230                 235                 240

Tyr Tyr Ala His Trp Lys Met Ser Glu Cys Val Asn Asn Ala Ala Gly
                245                 250                 255

Phe Gly Val Tyr Leu His Lys His Ser Gly Gln Thr Ser Trp Asp Gly
            260                 265                 270

Leu Ser Asp Gly Ser Val Leu Val Thr Glu Ala Ser Ser Arg Pro Ser
        275                 280                 285
```

```
Val Phe Ala Arg Lys Trp Asn Gln Thr Thr Val Asp Trp Leu Arg Lys
    290                 295                 300

Ile Val Phe Asn Arg Thr Ser Arg Ser Pro Leu Phe Met Thr Phe Gly
305                 310                 315                 320

Phe Ser Ala Leu Trp His Gly Leu His Pro Gly Gln Ile Leu Gly Phe
                325                 330                 335

Leu Ile Trp Ala Val Thr Val Gln Ala Asp Tyr Lys Leu His Arg Phe
                340                 345                 350

Leu His Pro Lys Leu Asn Ser Leu Trp Arg Lys Arg Leu Tyr Val Cys
                355                 360                 365

Val Asn Trp Ala Phe Thr Gln Leu Thr Val Ala Cys Val Val Val Cys
    370                 375                 380

Val Glu Leu Gln Ser Leu Ala Ser Val Lys Leu Leu Trp Ser Ser Cys
385                 390                 395                 400

Ile Ala Val Phe Pro Leu Leu Ser Ala Leu Ile Leu Ile Ile Leu
                405                 410                 415

<210> SEQ ID NO 28
<211> LENGTH: 1248
<212> TYPE: DNA
<213> ORGANISM: zebrafish

<400> SEQUENCE: 28
atgatagatc tcctttggat ttcttctgat ggacaccctc agctgtttta ccagtttatc      60
aacataccat ttgcatttct gtttcattgc ttatccagtc aaggacatct ctcgataatc     120
aacaggtacg tctatttggc gatgggagga ttcatgctgg ctattgcaac aatgggtcca     180
tatagctcac tgctgttcct gagtgctatt aaactgctgt tactgatcca ctatatacat     240
ccaatgcatc ttcatcggtg gattctggga ctgcagatgt gttggcaaac tgctggcat      300 ttgtacgtcc agtaccagat atactggctt caagaggcac cagactcaag cttttactg      360 gccatatctg cactcatgtt gatgacccag aggatttcct ctctatcact cgatttccaa     420
gaggggacga tctccaatca gtcaatcctt attccattcc taacctactc gctttatttc     480
cctgcccttc ttggaggtcc actttgcagt ttcaatgctt tgttcagtc tgtcgagcgt      540 caacacacca gcatgacttc atatttagga atctcactt caaagatatc acaagttata     600
gttttggtgt ggattaaaca gcttttcagt gagcttttga atctgccac gtttaacatc      660 gacagtgttt gtcttgatgt attgtggatt tggatctttt cgctgacact taggcttaat     720
tactatgcac actggaagat gagcgagtgt gttaataatg ctgcaggatt tggtgtctat     780
ttacacaaac acagtggaca acatcatgg gacggtcttt ctgatgggag tgtactggtg      840
actgaagcat ccagtcgtcc ttcggttttt gcgcgaaagt ggaaccaaac cacggtggat     900
tggcttcgaa aaatagtctt caacaggacc agcagatctc cactgttcat gacttttggg     960
ttttctgcac tgtggcacgg tcttcaccct gggcagattc tgggtttcct catttgggcc    1020
gtcactgtgc aggcggacta caaactgcat cgcttcttgc acccgaagct taactccctg    1080
tggagaaaac ggctgtatgt gtgtgtaaac tgggccttta ctcagctgac cgtcgcatgt    1140
gttgtggtct gtgtggagct tcagagtttg gcatcagtta agctgctctg gtcttcgtgt    1200
attgctgtgt ttccactgct gagtgctctg atcttaataa tcctctga                 1248
```

GHRELIN O-ACYLTRANSFERASE (GOAT) BIOCHEMICAL ASSAY

This work was supported by grants from the National Institutes of Health (HL20948); the Government has certain rights in this invention.

FIELD OF THE INVENTION

The field of the invention is ghrelin O-acyltransferase assays.

BACKGROUND OF THE INVENTION

The appetite-stimulating peptide hormone, ghrelin, is the only protein in animals that is known to be modified by O-acylation with octanoate, an eight-carbon fatty acid. Octanoylation is required for the endocrine actions of ghrelin, but no enzyme that catalyzes this novel modification has yet been identified (Kojima and Kangawa, 2005; van der Lely et al., 2004).

The discovery of ghrelin was reported in 1999 by Kojima et al. (Kojima et al., 1999), who were searching for a ligand for an orphan G-protein coupled receptor (GHS-R) that stimulates the secretion of growth hormone in the pituitary gland. The ligand was purified from rat stomach, and it was shown to stimulate the release of growth hormone from cultured pituitary cells. Kojima, et al. (1999) determined that the 28-amino acid ghrelin is derived proteolytically from a precursor of 117 amino acids. Analysis by mass spectroscopy revealed that serine-3 of ghrelin is modified by O-acylation with an octanoyl residue, which is required for growth hormone releasing activity. Serine-3 is conserved in mammals, birds, and fish. In the bullfrog serine-3 is replaced by threonine, but this residue is also octanoylated (Kaiya et al., 2001; Kojima and Kangawa, 2005). Thus, O-octanoylation of ghrelin has been conserved in vertebrates over millions of years of evolution.

Interest in ghrelin rose dramatically when it was demonstrated that ghrelin concentrations in human plasma rise immediately before mealtimes (Cummings, 2006; Small and Bloom, 2004). Moreover, infusion of ghrelin into the cerebral ventricles of rats markedly enhances food intake apparently through actions on the hypothalamus (Kamegai et al., 2001). Elimination of ghrelin or its receptor in mice through knockout technology caused a modest but significant reduction in obesity when the mice were presented with high fat diets (Wortley et al., 2005; Zigman et al., 2005). These findings aroused interest in ghrelin inhibitors as potential preventatives for obesity in humans.

One way to inhibit the action of ghrelin would be to block the supposed enzyme that attaches octanoate. An inhibitor should be quite specific since no other protein is known to be octanoylated. Thus far, however, a ghrelin octanoylating enzyme has escaped identification. In the current studies, we have identified the ghrelin-acylating enzyme.

The initial insight came from studies on the *Drosophila* wingless gene and its mammalian homolog, Wnt. Genetic studies in *Drosophila* had earlier demonstrated that Wingless activity required the action of another gene porcupine (Kadowaki et al., 1996). The amino acid sequence of Porcupine contains a conserved region that is found in a family of membrane-bound hydrophobic enzymes that transfer long-chain fatty acids to membrane-associated hydroxyl acceptors, called "MBOATs" for Membrane-Bound O-Acyltransferases (Hofmann 2000). Examples include acyl-CoA: cholesterol acyltransferases (ACATs), which attaches fatty acids to the hydroxyl group of cholesterol and diacylglycerol acyltransferases (DGATs), which acylate the hydroxyl group of diacylglycerol. Subsequent studies indeed showed that Porcupine is required for the attachment of a monounsaturated long-chain fatty acid to a serine residue in Wnt (Takada et al., 2006).

Here, we show that the mammalian genome encodes 16 MBOATs produced by 11 genes, and we show that one of these MBOATs catalyzes the octanoylation of ghrelin when it is expressed together with prepro-ghrelin in cultured mammalian endocrine cell lines. We name this enzyme GOAT (Ghrelin O-Acyltransferase).

CITED LITERATURE

Altschul, et al.(1997). Nucleic Acids Res. 25, 3389-3402.
Asfari, et al. (1992). Endocrinology 130, 167-178.
Bizzozero, O. A. (1995). Meth. Enzymol. 250, 361-379.
Chen, et al. (2004). Genes Dev. 18, 641-659.
Cummings, D. E. (2006). Physio. Behavior 89, 71-84.
Date, et al. (2000). Endocrinology 141, 4255-4261.
Hannah, et al. (2001). J. Biol. Chem. 276, 4365-4372.
Hofmann, K. (2000). TIBS 25, 111-112.
Kadowaki, et al. (1996). Genes Dev. 10, 3116-3128.
Kaiya et al. (2001). J. Biol. Chem. 276, 40441-40448.
Kaiya, et al. (2004). Gen. Comparative Endocrin. 138, 50-57.
Kamegai et al.(2001). Diabetes 50, 2438-2443.
Kapust, et al. (2001). Protein Eng. 14, 993-1000.
Karreman, C. (1998). BioTechniques 24, 736-742.
Kojima, et al. (1999). Nature 402, 656-660.
Kojima, M. and Kangawa, K. (2005). Physiol. Rev. 85, 495-522.
Miyazaki, et al. (1990). Endocrinology 127, 126-132.
Nishi et al. (2005). Endocrinology 146, 2255-2264.
Nohturfft, et al. (2000). Cell 102, 315-323.
Small, C. J. and Bloom, S. R. (2004). Trends Endocrin. Metabolism 15, 259-263.
Takada et al. (2006). Dev. Cell 11, 791-801.
van der Lely, et al. (2004). Endocrine Rev. 25, 426-457.
Walker, D. and Koonin, E. (1997). Intell. Sys. Mol. Biol. 5, 333-339.
Willert, et al. (2003). Nature 423, 448-452.
Wortley, et al. (2005) J. Clin. Invest. 115, 3573-3578.
Zhu, X., Cao, Y., Voodg, K., and Steiner, D. F. (2006). J. Biol. Chem. 281, 38867-38870.
Zigman, J. M. and Elmquist, J. K. (2006). Proc. Natl. Acad. Sci. USA 103, 12961-12962.
Zigman, et al. (2005). J. Clin. Invest. 115, 3564-3572.
Zorrilla, et al. (2006). Proc. Natl. Acad. Sci. USA 103, 13226-13231.

SUMMARY OF THE INVENTION

The invention provides methods and compositions for acylating ghrelin. In one embodiment, the invention provides a method of inhibiting acylation of ghrelin, comprising (a) combining recombinant ghrelin O-acyltransferase, ghrelin and octanoyl with an agent; and (b) detecting a resultant decrease in octanoylation of the ghrelin by the acyltransferase.

In a particular embodiment, the invention is practiced in an in vitro format, wherein the acyltransferase and ghrelin are in vitro, the octanoyl is provided in the form of labeled octanoyl-CoA, the agent is a small molecule candidate, and the detecting step detects a resultant decrease in covalent transfer of the labeled octanoyl to the ghrelin by the acyltransferase to identify the candidate as a ghrelin O-acyltransferase inhibitor.

In a particular embodiment, the method is practiced in a cell-based format, wherein the acyltransferase and ghrelin are expressed in a cell in a culture medium, the octanoyl is provided by delivering to the medium as labeled octanoate which is converted by the cell to labeled octanoyl-CoA, the agent is a small molecule candidate, and the detecting step detects a resultant decrease in covalent transfer of the labeled octanoyl to the ghrelin by the acyltransferase to identify the candidate as a ghrelin O-acyltransferase inhibitor.

In a more particular embodiment of the cell-based format, the acyltransferase is inducibly expressed in the cell, and the method further comprises the step of inducing expression of the acyltransferase.

The invention also provides compositions including (a) mixtures of isolated or recombinant ghrelin and isolated or recombinant ghrelin O-acyltransferase; (b) mixtures of defined amounts or concentrations of ghrelin and ghrelin O-acyltransferase; (c) mixtures of recombinant ghrelin and recombinant ghrelin O-acyltransferase; and (d) recombinant mammalian, particularly human, ghrelin O-acyltransferase.

The invention also provides recombinant expression constructs for the disclosed mammalian, particularly human ghrelin O-acyltransferases, which typically encode the acyltransferase operably linked to a heterologous promoter, and cells comprising such constructs.

DETAILED DESCRIPTION OF SPECIFIC
EMBODIMENTS OF THE INVENTION

In one embodiment, the invention provides a method of modulating acylation of ghrelin, which may be implemented as a drug screening or validation assay in cell-free (in vitro) or cell-based assay formats. In preferred embodiments, the assay is practiced with multiple candidate agents in parallel, preferably massive parallel, for high-throughput screening.

Generally these methods comprise the steps of: (a) combining recombinant ghrelin O-acyltransferase, ghrelin and octanoyl group with an agent; and (b) detecting a resultant decrease in octanoylation of the ghrelin by the acyltransferase. The form of the acyltransferase, ghrelin and octanoyl are selected to be compatible with the selected assay format, as described further below. For example, ghrelin encompasses alternative forms of ghrelin that provide operable substrates for the acyltransferase in the assay, including mature, processed ghrelin (residues 1-28), pro-ghrelin (including the C-terminal propeptide-residues 29-94), and prepro-ghrelin (including the 23-residue N-terminal signal sequence).

The combination of step (a) is incubated under conditions wherein but for the presence of the agent, the ghrelin O-acyltransferase catalyzes the specific transfer of a reference or control amount of octanoyl to the ghrelin. The detecting step then detects an agent-biased amount of octanoylation of the ghrelin, wherein a reduced agent-biased octanoylation of the ghrelin relative to the control or reference amount indicates that the agent is an inhibitor of ghrelin acylation. The detecting step is typically preceded by a wash step, which depending on the assay format, may be facilitated with a bead column, filter, etc. wherein unreacted (not ghrelin-attached), labeled octanoyl is removed.

In the in vitro format, the acyltransferase is recombinant and presented in membrane-bound or detergent-solubilized, active form, and often in a determined or quantified amount. Alternative protocols for isolating membrane-bound or detergent-solubilized active forms of the enzyme are readily practiced; see, e.g. Radhakrishnan et al., Mol. Cell. 15: 259-268, 2004; Radhakrishnan et al., PNAS USA 104: 6511-6518, 2007. The ghrelin is recombinant or synthetic pro-ghrelin, and often in a determined or quantified amount. The method may optionally comprise the antecedent step of recombinantly expressing and/or isolating, and/or solubilzing the acyltransferase, and may optionally comprise the antecedent step of recombinantly expressing or synthesizing, and/or isolating the ghrelin.

The octanoyl group is typically labeled (e.g. radio- or fluorescent-labeled) and presented in a transferable, high-energy form (e.g. octanoyl-CoA) to facilitate catalytic octanoylation. In an alternative embodiment, the ghrelin is labeled. The agent is typically a small molecule, assay compatible candidate, and it typically part of a library or panel of compounds screened in parallel. The detecting step generally detects a resultant decrease in covalent transfer of the labeled octanoyl to the ghrelin by the acyltransferase to identify the candidate as a ghrelin O-acyltransferase inhibitor.

In a particular embodiment, the method is practiced in scintillation proximity bead assay format, wherein the ghrelin is immobilized on a bead, and radiolabeled octanoylation of the ghrelin is detected by scintillation counts. In an alternative embodiment, the octanoyl moiety is immobilized, and the ghrelin is radiolabeled.

In the cell-based format, the acyltransferase and ghrelin are expressed in a cell in a culture medium. The cell type is discretionary, so long as it is compatible with the acylation assay. Both the acyltransferase and ghrelin (the prepro-ghrelin form) are expressed by the cell, and in a preferred embodiment, the acyltransferase is inducibly expressed in the cell, and the method further comprises the step of inducing expression of the acyltransferase with a corresponding inducer (e.g. tetracycline).

The octanoyl is provided by delivering to the medium labeled octanoate which is converted by the cell to labeled octanoyl-CoA. The agent is typically a small molecule, assay-compatible candidate, and it typically part of a library or panel of compounds screened in parallel. The detecting step generally detects a resultant decrease in covalent transfer of the labeled octanoyl to the ghrelin by the acyltransferase to identify the candidate as a ghrelin O-acyltransferase inhibitor.

The invention also provides compositions including (a) mixtures of isolated or recombinant ghrelin and isolated or recombinant ghrelin O-acyltransferase; (b) mixtures of defined amounts or concentrations of ghrelin and ghrelin O-acyltransferase; (c) mixtures of recombinant ghrelin and recombinant ghrelin O-acyltransferase; and (d) recombinant mammalian, particularly human, ghrelin O-acyltransferase.

The invention also provides recombinant expression constructs for the disclosed mammalian, particularly human ghrelin O-acyltransferases, which typically encode the acyltransferase operably linked to a heterologous promoter, and cells comprising such constructs. Methods for making recombinant ghrelin O-acyltransferase comprise culturing such cells under conditions whereby the enzyme is expressed, and optionally, isolating the enzyme.

Bioinformatic Identification and cDNA Cloning of Mouse MBOATs.

We identified sixteen members of the MBOAT family in the mouse genome, using reported MBOAT sequences (Hofmann, 2000) as queries and PSI-BLAST searches (E-value cutoff 0.005, default parameters) (Altschul et al., 1997) against the non-redundant mouse protein sequence database.

Full-length cDNAs for 15 of the 16 MBOATs were cloned by RT-PCR of total RNA isolated from the stomach of C57BL/6J mice that had been fasted for 16 hr. The cloned sequences with or without addition of sequences encoding a C-terminal Flag-tag or HA-tag were inserted into pcDNA3 or pcDNA3.1 vectors (Invitrogen) driven by the cytomegalovirus (CMV) promoter-enhancer. Primers for RT-PCR were designed according to the coding sequences available in the NCBI database. For each MBOAT without isoforms, 10 to 20 cDNA clones were sequenced in their entirety; for the three MBOATs with multiple isoforms (MBOAT1, MBOAT2, and porcupine), 60 to 80 cDNA clones were sequenced.

For one of the 16 MBOATs, we initially failed to clone a full-length cDNA. This MBOAT was designated in the NCBI database (May 2007) as "similar to O-acyltransferase (membrane bound) domain containing 1" (XM_134120). Efforts to clone its cDNA failed because the NCBI annotation at the 5' end was incorrect. As a result, the 5' primers failed to prime PCR amplification. We therefore synthesized an artificial cDNA according to the sequence of XM_134120. After obtaining four segments of DNA corresponding to nucleotides 1-391, 398-885, 907-1254, and 1261-1581 of XM_134120, we pieced them together by fusion-PCR (Karreman, 1998). On Jun. 20, 2007, the incorrect NCBI annotation of XM_134120 was replaced by two new annotations that were renamed MBOAT4, XM_001476434 and XM_001472220. These two versions of MBOAT4 differed from each other by 376 nucleotides at the 5'-end, and they differed from XM_134120 at the 5'-end in the following ways: XM_001476434 was 211 bp shorter than XM_134120 and XM_001472220 was 165 bp longer than XM_134120. To determine the correct 5'-end of the MBOAT4 mRNA, we carried out 5' rapid amplification of cDNA ends (5'-RACE) using total RNA from mouse stomach, 3' nested primers designed according to the sequence of the longer putative MBOAT4 transcript XM_001472220, and the FirstChoice RLM-RACE Kit (Ambion). The results showed that the correct annotation was XM_001476434. The current NCBI database (Nov. 27, 2007) contains partial DNA sequence information on 11 ESTs corresponding to XM_001476434. Of the 11 ESTs, only one of them (IMAGE 5655946) extends to the 5'-end. This sequence corresponds to the cDNA that we subsequently showed to encode ghrelin O-acyltransferase (GOAT).

A full-length cDNA for mouse GOAT was generated by RT-PCR of total stomach RNA as described above. The chimpanzee ortholog (XP_519692) of mouse GOAT was identified by a "blastp" analysis of the non-redundant protein database. Orthologs of GOAT in other species were found by clustering identified genomic sequences with the SEALS command grouper (with criterion −1scut=0.6) (Walker and Koonin, 1997). In genomic DNA from several species, the annotation of exons did not permit this determination of the amino acid sequence at the N-terminus of the proteins. In these cases we used the N-terminal amino acid sequence translated from mouse cDNA as a query, which allowed us to identify complete GOAT ortholog amino acid sequences through the use of tblastn searches. The reference numbers for the corresponding genomic DNA sequences were as follows: rat (NW_047474.1), human (NT_007995.14), bovine (NW_001494415.1), horse (NW_001799700.1), and zebrafish (NW_001513480.1). Alignments were carried out by ClustalW. cDNA sequences and translates for representative animal GOAT species are appended hereto.

Cell Culture and Transient Transfection.

All cells were grown in monolayer at 37° C. in an atmosphere of 8.8% $CO_2$. Mouse AtT-20 cells were cultured in medium A (Dulbecco's modified Eagle's medium (4.5 g/L glucose) supplemented with 2 mM glutamine, 10% (v/v) fetal calf serum (FCS), 100 U/ml penicillin, and 100 µg/ml streptomycin). INS-1 cells (Asfari et al., 1992) were cultured in medium B (RPMI 1640 medium supplemented with 10% FCS, 10 mM Hepes, 50 µM β-mercaptoethanol, 100 U/ml penicillin, and 100 µg/ml streptomycin). MIN-6 cells (Miyazaki et al., 1990) were cultured in medium C (Dulbecco's modified Eagle's medium (4.5 g/L glucose) supplemented with 10% FCS, 10 mM Hepes, 50 µM β-mercaptoethanol, 100 U/ml penicillin, and 100 µg/ml streptomycin).

For transient transfections, AtT-20 cells were set up on day 0 at $1 \times 10^6$ per 100-mm dish; INS-1 cells and MIN-6 cells were set up at $1.5 \times 10^6$ per 100-mm dish. On day 2, cells were transfected with plasmids using FuGENE HD Transfection Reagent (Roche) at a ratio of FuGENE HD to plasmids of 3:1. On day 3 or 4, cells were subjected to various treatments described herein. On day 4 or 5, cells were harvested for experiments. The total amount of transfected DNA in each experiment was constant and adjusted to 5 or 6 µg per 100-mm dish by addition of pcDNA3.1 mock vector.

Generation of Anti-Ghrelin Antibody

DNA segments encoding mouse pro-ghrelin and ghrelin were cloned into pGEX-4T1 (GE Healthcare) to generate glutathione S-transferase (GST)-fusion proteins. For the GST-pro-ghrelin construct, the thrombin cleavage site within the vector sequence (LVPRGS) between GST and pro-ghrelin was changed to the Tobacco Etch Virus (TEV) protease site (ENLYFQG) (Kapust et al., 2001), and a $His_8$-tag was added to the C-terminus of pro-ghrelin. GST-pro-ghrelin-$His_8$ and GST-ghrelin were expressed in E. coli and purified using glutathione-agarose beads. GST-pro-ghrelin-$His_8$ was cleaved by recombinant TEV protease (produced in E. coli as a GST fusion protein) to release pro-ghrelin-$His_8$, which was further purified by nickel-affinity chromatography (Qiagen). For immunization, each rabbit was injected subcutaneously with 500 µg GST-ghrelin in incomplete Freund's adjuvant, followed by sequential booster injections of 250 µg GST-ghrelin and 250 µg pro-ghrelin-$His_8$, both given subcutaneously in incomplete Freund's adjuvant. The resulting rabbit anti-ghrelin antiserum recognized pro-ghrelin and ghrelin in both the desacylated and acylated forms.

Peptide Extraction from Cultured Cells.

Peptides were extracted from cultured cells using the protocol described by Kojima et al (Kojima et al., 1999). After harvesting, the cell pellet was boiled in 1-2 ml of $H_2O$ for 10 min to inactivate proteases and then cooled on ice, after which acetic acid and HCl were added directly to achieve final concentrations of 1 M and 20 mM, respectively. The cell lysate was further disrupted by passage through a 22-gauge needle 10 times, followed by centrifugation at 20,000 g for 10 min at 4° C. The resulting supernatant was concentrated under vacuum to ~20% of the original volume, subjected to 67% (v/v) acetone precipitation, and centrifuged at 20,000 g for 10 min at 4° C. to remove the precipitate. The supernatant was evaporated under vacuum, and the residue was solubilized for SDS-PAGE and immunoblot analysis or reverse-phase chromatography followed by SDS-PAGE and immunoblot analysis as described below.

Immunoblot Analysis of Pro-Ghrelin and Ghrelin

The pellet containing the extracted peptides was dissolved in SDS-PAGE loading buffer (0.1 M Tris-chloride at pH 6.8, 5% (w/v) SDS, 0.1 M dithiothreitol, and 5% (v/v) glycerol), subjected to 16% Tricine SDS-PAGE, and then transferred to Immobilon-P PVDF membranes (Millipore) for immunoblot analysis. To prevent the diffusion of ghrelin during the blotting procedure, we washed each membrane three times with Phosphate-Buffered Saline (PBS) containing 0.05% Tween-20 (Sigma), after which the membrane was fixed at room temperature for 15 min in 50 mM Hepes-NaOH (pH 7.4) containing 2.5% (v/v) glutaraldehyde. The membrane was washed three times with the PBS/Tween-20 solution and then immunoblotted with either a 1:1000 dilution of anti-ghrelin antiserum or 0.5 μg/ml of anti-Flag M2 monoclonal antibody. Bound antibodies were visualized by chemiluminescence using a 1:10,000 dilution of either donkey anti-rabbit IgG or donkey anti-mouse IgG conjugated to horseradish peroxidase. All membranes were exposed to Phoenix Blue X-ray film for 5 sec to 2 min at room temperature.

Separation of Desacyl-Ghrelin and Acyl-Ghrelin by Reverse-Phase Chromatography

The residue after evaporation of the acetone was dissolved in 3 ml of 2% (v/v) $CH_3CN$ in 0.1% (v/v) trifluoroacetic acid (TFA) and loaded onto a 360-mg Sep-Pak C18-cartridge (Waters). The cartridge was washed with 3 ml of 2% $CH_3CN$ in 0.1% TFA and eluted with a step-gradient consisting of 6 ml of solution containing 20%, 40%, and ~80% $CH_3CN$ in 0.1% TFA. The first 3 ml of each 6-ml elution were collected and evaporated under vacuum, and the residue was dissolved in 80 μl of SDS-PAGE loading buffer, and aliquots of 20 μl were subjected to SDS-PAGE and immunoblot analysis as described above.

Hydroxylamine Treatment

After evaporation of the 40%-$CH_3CN$ fraction from reverse-phase chromatography, the residue was suspended in 0.4 ml of solution containing 20 mM Tris-chloride (pH 8.0), 100 mM NaCl, 1 mM sodium EDTA, and Protease Inhibitors Cocktail (Roche). An aliquot of each sample (0.2 ml) was mixed with 0.2 ml of either 2 M Tris-chloride (pH 8.0) or 2 M hydroxylamine (pH 8.0) and then rotated at room temperature for 2 hr, after which the reaction was stopped by adding 0.5 ml of 1 M acetic acid. The sample was further diluted in 10 ml of 2% $CH_3CN$ in 0.1% TFA and then subjected to reverse-phase chromatography as described above.

N-Terminal Sequencing of Pro-Ghrelin and its C-Terminal Peptide

INS-1 cells transfected with a cDNA encoding preproghrelin containing a C-terminal Flag-tag were harvested by scraping on day 4 and washed once with PBS. Cells from 30 100-mm dishes were solubilized in PBS containing 0.1% (v/v) Triton X-100, 1 mM sodium EDTA, and Protease Inhibitor Cocktail. After centrifugation at 100,000 g for 30 min at 4° C., a small aliquot of the supernatant (~1%) was subjected to SDS-PAGE and immunoblotted with anti-Flag M2 monoclonal antibody. The remainder of the supernatant was treated with 100 μl of anti-Flag M2 Affinity Gel. After overnight incubation at 4° C., the bound proteins were eluted by heating the gel at 95° C. for 5 min in 25 mM Tris-Chloride (pH 6.8) containing 1% SDS. After centrifugation at 20,000g for 5 min, an aliquot of the supernatant (25% of total) was loaded onto a 16% Tricine SDS-PAGE gel. After electrophoresis, proteins were transferred to an Immobilion-P$^{SQ}$ PVDF membrane (Millipore) and stained with 0.1% (w/v) amido black in 5% (v/v) acetic acid. After destaining with 5% acetic acid, appropriate bands were excised from the membrane and subjected to Edman degradation using the Procise 494 Protein Sequencing System (Perkin-Elmer).

[$^3$H]Octanoate Autoradiography and Identification of [$^3$H] Fatty Acid

[$^3$H]Octanoate-labeled INS-1 cells were processed as described herein and then subjected to autoradiography with a Kodak Transcreen LE Intensifying Screen and Biomax MS Film at −80° C. for 5 days. Radioactivity in the PVDF membrane was quantified by cutting each lane into 9 consecutive pieces from top to bottom, followed by liquid scintillation counting in 10 ml of counting cocktail (3a70B™, Research Products International Corp.).

To confirm the identity of the $^3$H-labeled fatty acid linked to pro-ghrelin and ghrelin, fatty acid methyl ester (FAME) analysis was carried out. Two dishes of transfected cells were radiolabeled with [$^3$H]octanoate. After reverse-phase chromatography, proteins in the 40%-$CH_3CN$ fraction were subjected to SDS-PAGE and transferred to a PVDF membrane. The pieces of membrane containing $^3$H-labeled pro-ghrelin and ghrelin were cut out, pooled together, and treated with 0.5 ml of 0.1 M KOH in 100% methanol at room temperature for 2 hr to form FAME. After acidifying the sample with 0.5 ml of 1.0 M HCl, the aqueous phase was extracted twice with 0.1 ml hexane. An aliquot of the pooled organic phase (50 μl) was mixed with 50 μg of each FAME standard (methyl hexanoate, methyl octanoate, methyl decanoate, methyl dodecanoate, methyl myristate, and methyl palmitate) and loaded onto a C18 reverse-phase thin-layer chromatography (TLC) plate (150 μm, 10×10 cm, Analtech). The TLC plate was developed in a solvent system of acetone/methanol/water (80:20:10, v/v/v), and FAME standards were revealed by iodine vapor counter-staining. The lane of TLC was divided into strips numbered 1 to 14 from the origin to the front, with strips 6 to 11 containing FAME standards. The resin on each strip was then scraped off and subjected to liquid scintillation counting as described above.

GOAT mRNA Expression in Mouse Tissues

Six-month old male C57BL6/J mice were fed a chow diet ad libitum prior to study. At the end of the dark phase, mice were anesthetized and exsanguinated. Various tissues were collected, snap-frozen in liquid nitrogen, and stored at −80° C. The stomach, small intestine, and colon were flushed with cold PBS, after which the intestine was divided into three equal lengths, designated duodenum (proximal), jejunum (medial), and ileum (distal). Each flushed segment of the gastrointestinal tract was cut open with a small scissors, and the mucosa was carefully scraped off and placed in a tube for RNA preparation. Total RNA was prepared from mouse tissues using an RNA STAT-60 kit from Tel-Test Inc. (Friendswood, Tex., USA). Equal amounts of RNA from four mice were pooled and analyzed for mRNA expression of GOAT, ghrelin, and β-actin using the TITANIUM™ One-Step RT-PCR Kit (Clontech). Each reaction contained 1 μg of pooled total RNA isolated from different mouse tissues as described above and primers. The cycling parameters were set as 94° C., 30 sec; 60° C., 30 sec; and 68° C., 30 sec. Number of cycles for GOAT, ghrelin, and β-action was 35, 30, and 25, respectively. Aliquots (20 μl) of the 50-μl RT-PCR samples were loaded onto 1.5% agarose gel.

Exemplary Results

We determined the conserved sequences in the putative catalytic domains of mammalian proteins that belong to the MBOAT family. These 11 catalytic domains are found in 16 MBOAT proteins since two of the encoding genes give rise to 2 isoforms and one gives rise to 4 isoforms as a result of alternative splicing. We identified these sequences through a search of genomic databases (herein). These enzymes are postulated to transfer fatty acyl groups to hydroxyl or sulfhydryl groups, forming ester or thio-ester bonds. Among the known substrates are lipids such as cholesterol and diacylglycerol. At least one protein, Wnt, is thought to be a substrate by virtue of a serine that is acylated (Takada et al., 2006). As described below, MBOAT4 mediates the octanoylation of ghrelin, and hence it is designated GOAT. The substrates for seven of the putative MBOATs (MBOAT1-a/b, MBOAT2-a/b, MBOAT5, LRC4, and GUP1) remain unknown.

We prepared a hydropathy plot of mouse GOAT. The sequence indicates eight transmembrane segments, a finding in keeping with the sequences of other MBOATs, all of which have multiple membrane-spanning helices. The GOAT sequence is highly conserved in mammalian and avian species, and a close relative is found in zebrafish. The putative catalytic asparagine and histidine residues are conserved throughout.

As a first step in identifying the enzyme that octanoylates ghrelin, we sought to identify cultured cells that process pro-ghrelin to ghrelin. For this purpose we produced prepro-ghrelin in a variety of cultured cell lines through cDNA transfection. Prepro-ghrelin contains 117 amino acids (Kojima and Kangawa, 2005). Cleavage of the 23-amino acid signal sequence yields pro-ghrelin which has glycine as its N-terminal residue, hereafter designated residue 1. The C-terminus of mature ghrelin is generated by prohormone convertase ⅓, which cleaves after arginine-28 of pro-ghrelin, generating the mature 28-amino acid peptide (Zhu et al., 2006).

After transfection, cell extracts were subjected to SDS-PAGE and immunoblotted with a polyclonal antibody that we raised against mouse ghrelin. All of the transfected cells produced an immunoreactive peptide with an apparent molecular mass of 12 kDa that corresponds to pro-ghrelin with the signal sequence removed. Three endocrine cell lines—mouse pituitary AtT-20 cells, rat insulinoma INS-1 cells, and mouse insulinoma MIN-6 cells—all produced a smaller peptide with an apparent molecular mass of 3 kDa that corresponds to ghrelin. Two non-endocrine cell lines—human kidney HEK-293 cells and Chinese hamster ovary (CHO-7) cells—failed to produce mature ghrelin.

To confirm that the mature ghrelin band resulted from cleavage at arginine-28 of pro-ghrelin, we prepared cDNAs encoding mutant forms of prepro-ghrelin with amino acid substitutions at or near arginine-28. The cDNAs were transfected into INS-1 cells, and mature ghrelin was identified by SDS-PAGE and immunoblotting. Replacement of arginine-28 with either lysine or leucine abolished cleavage, whereas replacement of residue 26 or 27 with an arginine reduced cleavage, but did not abolish it.

To further confirm the sites of cleavage that generate ghrelin, we prepared a cDNA encoding prepro-ghrelin with a Flag-tag at the C-terminus. We introduced this cDNA into INS-1 cells and isolated the Flag-tagged peptides by adherence to an immunoaffinity gel. SDS-PAGE was used to separate the Flag-tagged pro-ghrelin and the Flag-tagged C-terminal peptide that was generated after cleavage at arginine-28 of ghrelin. The separated peptides were then transferred to PVDF membranes and processed for Edman degradation. The N-terminal sequence of pro-ghrelin was GSSFL, which is consistent with cleavage of the signal sequence at the position determined herein. The N-terminal sequence of the smaller fragment, ALEG, is consistent with cleavage after arginine-28 of ghrelin. Considered together, these data indicate that the INS-1 cells process prepro-ghrelin at the correct sites to produce authentic mature ghrelin.

We next developed a reverse-phase chromatographic procedure to separate octanoylated ghrelin from desacyl-ghrelin. For use as standards, we purchased synthetic octanoylated and desacyl-ghrelin (herein). The peptides were applied to a C18 reverse-phase cartridge and eluted with a step-gradient of 20%, 40%, and 80%-$CH_3CN$ in 0.1% TFA. The eluted peptides were subjected to SDS-PAGE and immunoblotted with anti-ghrelin. Desacyl-ghrelin was eluted in the 20%-$CH_3CN$ fraction, and octanoyl ghrelin was eluted in the 40%-$CH_3CN$ fraction. To determine whether any of the endocrine cell lines could produce octanoylated ghrelin, we transfected the cells with a cDNA encoding prepro-ghrelin and subjected the extracted peptides to reverse-phase chromatography All of the ghrelin peptides were eluted in the 20%-$CH_3CN$ fraction, indicating that none of them was octanoylated.

We performed a series of experiments designed to determine whether any of 16 MBOATs were capable of producing octanoylated ghrelin when expressed with prepro-ghrelin in INS-1 cells. We first prepared cDNAs encoding each of the MBOATs with a C-terminal Flag-tag. When transfected into INS-1 cells, all of these cDNAs produced MBOAT protein that could be detected by SDS-PAGE and immunoblotting with anti-Flag. These cDNAs were then transfected into INS-1 cells together with a cDNA encoding prepro-ghrelin. The ghrelin peptides were extracted and subjected to reverse-phase chromatography. GOAT was the only MBOAT that produced acylated ghrelin, which was detected as a 3-kDa band that emerged in the 40%-$CH_3CN$ fraction. To confirm the acylating activity of GOAT, we repeated the co-transfection experiment. When the prepro-ghrelin cDNA was transfected together with a control cDNA (pcDNA3.1), ghrelin emerged in the 20%-$CH_3CN$ fraction, indicating a lack of acylation. We noted that pro-ghrelin emerged in the 40% and 80%-$CH_3CN$ fractions even though it was presumably not acylated. We attribute this to the known tendency of longer peptides to adhere to reverse-phase resins. When the GOAT cDNA was transfected, approximately half of the ghrelin emerged in the 40%-$CH_3CN$ fraction, indicating acylation. The elution pattern of pro-ghrelin was the same as in the control cells transfected with pcDNA3.1.

The activity of GOAT was not restricted to INS-1 cells. Expression of GOAT led to acylation of ghrelin in each of the three endocrine cell lines that were capable of processing pro-ghrelin to ghrelin. Our data confirm that the GOAT protein was expressed in the three transfected cell lines.

To confirm that ghrelin was acylated by GOAT, we tested the lability of the modification to hydroxylamine treatment, which is known to release ester-bound fatty acids from proteins (Bizzozero, 1995). When synthetic octanoylated ghrelin was treated with 1 M hydroxylamine (pH 8) the peptide no longer eluted from the reverse-phase cartridge in the 40%-$CH_3CN$ fraction. Treatment with 1 M Tris-chloride (pH 8) had no such effect. We determined the results of hydroxylamine treatment of peptide extracts obtained from INS-1 cells transfected with cDNAs encoding prepro-ghrelin and GOAT. When treated with 1M Tris-chloride, ghrelin eluted from the reverse-phase cartridge in the 40%-$CH_3CN$ fraction, but when treated with 1 M hydroxylamine it reverted to the 20%-$CH_3CN$ fraction, indicating that it had been deacylated.

Octanoylation of ghrelin in vivo is known to occur at serine-3 of the peptide. Mutation of serine-3 to alanine prevented acylation by GOAT, indicating that GOAT acylates the physiologic serine residue. Replacement of serine-3 with threonine preserved acylation, a finding consistent with the observation that this position is occupied by an octanoylated threonine in bullfrog ghrelin (Kaiya et al., 2001). Substitution of alanine for other serines in ghrelin (residues 2, 6, and 18) did not affect acylation.

Bioinformatic analysis (supra) proposed that the catalytic residues in mouse GOAT would be asparagine-307 and histidine-338. Our data demonstrate that both of these residues are required in order for GOAT to modify ghrelin. Substitution of either of these residues with alanine abolished GOAT's ability to acylate ghrelin. Another mutation (cysteine-181 to alanine) had no effect. We determined that all of the GOAT cDNAs were expressed at similar levels in the transfected cells.

To confirm that GOAT modifies ghrelin with octanoate, we transfected INS-i cells with cDNAs encoding prepro-ghrelin, and wild-type or mutant version of GOAT. The cells were incubated with [$^3$H]octanoate, and the extracted peptides were subjected to reverse-phase chromatography. Each 40%-

CH₃CN fraction was subjected to SDS-PAGE, after which the radiolabeled peptides were transferred to duplicate PVDF membranes. One membrane was subjected to immunoblot analysis with anti-ghrelin, demonstrating that pro-ghrelin was present in all lanes while ghrelin was detected only in lane 2. The other membrane was subjected to autoradiography to visualize the labeled proteins. For quantification, each lane of the membrane was cut into 9 slices, which were then subjected to scintillation counting. When the cells were transfected with the GOAT cDNA, labeled peptides were observed in the position of pro-ghrelin and ghrelin. As expected, no radioactivity was incorporated into the S3A mutant of ghrelin. Lane 4 shows the result when prepro-ghrelin contained leucine in place of arginine at the residue corresponding to position 28 of ghrelin. This substitution prevents the cleavage of pro-ghrelin to ghrelin. In this case, we observed radiolabeling of the pro-ghrelin band, but there was no ghrelin band. We observed no labeled band when the cells were transfected with a cDNA encoding a catalytically inactive mutant of GOAT (H338A). As a further control, we found that transfection of a cDNA encoding another MBOAT (MBOAT1-a) failed to produce a radiolabeled band.

To confirm that the cells had incorporated [$^3$H]octanoate without changing its length, we removed the labeled fatty acid from the protein by methanolysis and subjected the methyl ester to thin-layer chromatography (TLC) in a system that separates fatty acid methyl esters according to chain length. Scintillation counting of the TLC plate confirmed that the material attached to pro-ghrelin and ghrelin was the eight-carbon [$^3$H]octanoate.

Finally, we used semi-quantitative PCR to compare the levels of GOAT and prepro-ghrelin mRNAs in various tissues of the mouse. As previously reported (Kojima et al., 1999), prepro-ghrelin mRNA was expressed most highly in the stomach followed by the intestine. There was very little expression in other tissues. Likewise, GOAT mRNA was highest in stomach, and detectable in the small intestine and colon, but not in other tissues. In stomach, we noted that the amount of GOAT mRNA appeared to be much lower than the amount of prepro-ghrelin mRNA. Even after 35 cycles of PCR, the intensity of the amplified GOAT product was less than that observed with prepro-ghrelin after only 30 cycles. This relative difference of ~200-fold was confirmed in experiments using quantitative RT-PCR. In vitro octanoylation assay GOAT-Ghrelin Acylation Assays To facilitate screening for GOAT-ghrelin acylation inhibitors, we developed specific acylation assays. In one embodiment, enriched membranes stimulate the octanoylation of recombinant pro-ghrelin when incubated with [$^3$H]octanoyl CoA as a source of the [$^3$H]octanoyl group. When the assay contained membranes from INS-1 cells that had been transfected with GOAT cDNA, the amount of $^3$H-radioactivity covalently linked to pro-ghrelin increased 5-fold above the background observed in assays containing membranes from mock-transfected INS-1 cells. No such increase was seen when the S3A mutant version of pro-ghrelin was incubated with wild-type GOAT-containing membranes or when wild type pro-ghrelin was incubated with membranes enriched in the catalytically impaired H338A mutant version of GOAT.

The acylating activity of GOAT could also be reconstituted in vitro using membranes from Sf9 insect cells that had been infected with baculovirus encoding GOAT cDNA. When wild-type pro-ghrelin was used as a substrate, the amount of [$^3$H]octanoyl pro-ghrelin formed was more than 5-fold higher than when the S3A mutant pro-ghrelin was used as the substrate. The acylating activity of GOAT in the membranes of Sf9 insect cells was ~5-fold higher than that of INS-1 cells.

GOAT Acylation Assay Protocols

Each assay tube, in a final volume of 50 µl, contained 50 mM Tris-chloride at pH 7.0, 2 mM Na-ATP, 5 mM MgCl₂, 1 mM Na-EDTA, 160 µg of membrane proteins from either INS-1 cells or Sf9 cells (see below), 5 µg recombinant wild-type or mutant pro-ghrelin-His₈ (see below), and [$^3$H-2,2',3,3']octanoyl CoA (132 dpm/fmol, American Radiolabeled Chemicals). The tubes were sonicated in a water-bath sonicator at 4° C. for 1 min, followed by incubation at 30° C. for 30 min. Reactions were stopped by addition of 1 ml of buffer A (50 mM Tris-chloride at pH 7.5, 150 mM NaCl, and 0.1% (w/v) Fos-choline 13). After centrifugation at 20,000 g for 5 min at 4° C., each supernatant was loaded onto a 0.2-ml nickel affinity column to retrieve the [$^3$H]octanoyl-labeled pro-ghrelin. The column was washed three times with 1 ml of buffer A containing 50 mM imidazole, followed by elution with 1 ml of buffer A containing 250 mM imidazole. Radioactivity present in the eluate was counted by liquid scintillation as described above under "[$^3$H]Octanoate Autoradiography and Identification of [$^3$H]Fatty Acid."

Recombinant wild-type and S3A mutant version of pro-ghrelin-His₈ were produced as GST-fusion proteins described above under "Generation of Anti-Ghrelin Antibody." After removal of the GST by cleavage with TEV protease, the His₈-tagged wild-type and mutant pro-ghrelins were purified by nickel-affinity chromatography and stored at −80° C. at a stock concentration of 1 mg/ml in 10 mM Tris-chloride at pH 8.5, 50 mM NaCl, 10% (v/v) glycerol, and 0.01% (w/v) CHAPS.

Two sources of membrane proteins containing GOAT were used in the above in vitro assay—one prepared from INS-1 cells transfected with GOAT cDNA and the other from Sf9 insect cells infected with baculovirus containing GOAT cDNA. INS-1 cells were set up for experiments on day 0 as described above under "Cell Culture and Transient Transfection." On day 2, cells were transfected with 5 µg pcDNA3.1 or 5 µg of a cDNA encoding wildtype or H338A mutant version of mouse GOAT. On day 5, cells were harvested, and after washing once with PBS, the cell pellets were frozen at −80° C. Sf9 insect cells were infected at a density of 1×10⁶/ml with baculovirus containing GOAT cDNA. Cells were harvested 48 hr post-infection, and after washing once with PBS, the cell pellets were frozen at −80° C. Procedures for insertion of GOAT cDNA into pFastBac HT-A (His₁₀-tag), generation of baculovirus, and culture of Sf9 cells were carried out by standard methods (see Radhakrishnan, et al. 2004, Mol. Cell. 15, 259-268.).

Each pellet of INS-1 cells or Sf9 cells was homogenized on ice in 50 mM Tris-chloride at pH 7.0, 1 mM Na-EDTA, and 40 µg/ml phenylmethanesulfonyl fluoride (PMSF) by passing through a 22-gauge needle for 30 times. After an initial centrifugation at 1,000 g for 5 min at 4° C., the supernatant was centrifuged at 20,000 g for 10 min at 4° C. The resulting membrane fraction (20,000 g pellet) from five 100-mm dishes of INS-1 cells or 20 ml of Sf9 cell culture was resuspended in 0.2 ml of homogenizing buffer.

The foregoing description and examples are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill

APPENDIX cDNA and Protein Sequences of GOATs from 6 Mammals and Zebrafish

Sequences were deduced by the tblatn program from NCBI genomic databases queried with the experimentally determined mouse GOAT protein sequence shown below.

Of the 7 GOAT protein sequences from the 7 species shown below, only 2 of these sequences in the RefSeq NCBI database (mouse and chimpanzee) matched the N-terminus of our cloned and experimentally active mouse GOAT sequence. The other 5 sequences (from rat, human, bovine, horse, and zebrafish) showed N-termini inconsistent with the mouse start in that they lacked the N-terminal segments containing the first ~50 to 100 amino acids. Apparently, the software for prediction of coding regions missed the first one or two coding exons in these 5 species. However, tblastn searches of genomic assemblies from each of these 5 species revealed the missing N-terminal segments for all 5 sequences, each of which exhibited high sequence similarity to the mouse GOAT sequence.

Here, we list the complete protein sequences for mouse, rat, human, chimpanzee, bovine, horse, and zebrafish, and we provide DNA sequences for the coding exons of the 5 species whose N-terminal regions in RefSeq NCBI protein database are apparently incorrect.

Mouse

Experimentally Determined Mouse cDNA (Method for Obtaining Correct cDNA Described in Patent)

sequence after the stop codon is not included, start codon is shown in bold letters GACTTCCCTTTTACAAGGGCACCGCT-
TAGGGACTCTAGGAAGGACAGTGGGCCT-
CACATTCAGGATGGATTGGCTC-
CAGCTCTTTTTTCTGCAT
CCTTTATCATTTTATCAAGGGGCTGCAT-
TCCCCTTTGCGCTTCTGTTTAAT-
TATCTCTGCATCTTGGACACCTTTTC-
CACCCGGGCCAGGTACC
TCTTTCTCCTGGCTGGAGGAGGTGTC-
CTGGCTTTTGCTGCCATGGGTC-
CCTACTCTCTGCTCATCTTCATCCCT-
GCGCTCTGCGCTGTGGCTCT
GGTCTCCTTCCTCAGTCCACAGGAAGTC-
CATAGGCTGACCTTCTTCTTTCA-
GATGGGCTGGCAGACCCTGTGC-
CATCTGGGTCTTCACTACACC
GAATACTACCTGGGTGAGCCTCCAC-
CCGTGAGGTTCTACATCACTCTTTCTTC-
CCTCATGCTCTTGACGCAGAGAGTCA-
CATCCCTCTCACTGG
ACATTTGTGAAGGGAAGGTGGAGGC-
CCCGAGGCGGGGCATCAGGAGCAAGAGT-
TCTTTCTCTGAGCACCTGTGGGATGCTC-
TACCTCATTTCAG
CTACTTGCTCTTTTTCCCTGCTCTC-
CTGGGAGGCTCCCTGTGTTCCTTCCG-
GAGGTTTCAGGCTTGCGTTCAAAGAT-
CAAGCTCTTTGTATCCG
AGTATCTCTTTTCGGGCTCTGACCTG-
GAGGGGTCTGCAGATTCTCGGGCTG-
GAGTGCCTCAAGGTGGCGCTGAG-
GAGCGCGGTGAGTGCTGGAG
CTGGACTGGATGACTGCCAGCGGCTG-
GAGTGCATCTACCTCATGTGGTCCA-
CAGCCTGGCTCTTTAAACTCACCTAT-
TACTCCCATTGGATCCT
GGACGACTCTCTCCTCCACGCG-
GCGGGCTTTGGCGCTGAGGCTGGC-
CAGGGGCCTGGAGAGGAGGGATACGTC-
CCCGACGTGGACATTTGGACC
CTGGAAACTACCCACAGGATCTCCCTGT-
TCGCCAGGCAGTGGAACCGAAGCA-
CAGCTCTGTGGCTCAGGAGGCTCGTCT-
TCCGGAAGAGCCGGC
GCTGGCCCCTGCTGCAGACATTTGCCT-
TCTCTGCCTGGTGGCACGGGCTCCAC-
CCAGGTCAGGTGTTCGGCTTCCTGT-
GCTGGTCTGTAATGGT
GAAAGCCGATTATCTGATTCA-
CACTTTTGCCAACGTATGTATCAGATC-
CTGGCCCCTGCGGCTGCTTTATAGAGC-
CCTCACTTGGGCTCATACC
CAACTCATCATTGCCTACATCATGCTG-
GCGGTGGAGGGCCGGAGCCTTTC-
CTCTCTCTGCCAACTGTGCTGTTCTTA-
CAACAGTCTCTTCCCTG
TGATGTACGGTCTTTTGCTTTTTCTGT-
TAGCGGAGAGAAAASACAAACGTAACGA (SEQ ID NO:01)

Protein Sequence

>gi|149258535|ref|XP_001476484.1| PREDICTED: similar to FKSG89 [*Mus musculus*]

MDWLQLFFLHPLSFYQGAAFPFALLF-
NYLCILDTFSTRARYLFLLAGGGV-
LAFAAMGPYSLLIFIPALCA VALVSFLSPQEVHRLT-
FFFQMGWQTLCHLGLHYTEYYLGEPPPVRFYITLSS-
LMLLTQRVTSLSLDICEG KVEAPRRGIRSKSSFSEHL-
WDALPHFSYLLFFPALLGGSLCSFRRFQACVQR-
SSSLYPSISFRALTWRGL QILGLECLKVALRSAVSA-
GAGLDDCQRLECIYLMWSTAWLFKLTYY-
SHWILDDSLLHAAGFGAEAGQGPG EEGYVPDVDI-
WTLETTHRISLFARQWNRSTALWLRRLVFRKSRRWP-
LLQTFAFSAWWHGLHPGQVFGFLC WSVMVKADY-
LIHTFANVCIRSWPLRLLYRALTWAHTQLIIAYIMLAV-
EGRSLSSLCQLCCSYNSLFPVMY GLLLFLLAERKD-
KRN (SEQ ID NO:02)

Rat

Coding DNA Region in 3 Exons

>ref |NW_047474.1 |Rn16_WGA1996_4:c1695518-1695399 *Rattus norvegicus* chromosome 16 genomic contig, reference assembly (based on RGSC v3.4)

ATGGATTGGCTCCAGTTCTTCTTTCTCCATCCTGT-
ATCACTTTATCAAGGGGCTGCTTTCCCCTTCGCGC
TTCTGTTTAATTATCTCTGCATCACGGAATCCTTT-
CCCACCCGGGCCAGG (SEQ ID NO:03)>

>ref |NW_047474.1 |Rn16_WGA1996_4:c1690789-1690565 *Rattus norvegicus* chromosome 16 genomic contig, reference assembly (based on RGSC v3.4)

TACCTCTTTCTCCTGGCTGGAGGAGGT-
GTCCTGGCTTTGGCCGCCATGGGTC-

CCTACGCTCTGCTCATTT TCATCCCSGCTCTCSGSGCCGSGGCTASGATCTCCTCCCTCAGSCCACAGGAAGSCCASGGGCSGACTTT CTTCTTTCAGATGGGTTGGCAAACCCTGTGCCACCTGGGTCTTCACTACAAGGAGTACTACCTGTGTGAG CCTCCCCCTGTGAGG (SEQ ID NO:04)

>ref |NW_047474.1 |Rn16_WGA1996_4:c1688186-1687224 *Rattus norvegicus* chromosome 16 genomic contig, reference assembly (based on RGSC v3.4) TTCTACATCACCTTTTCTTCCCTCATGCCTTTGACGCAGAGAGTCACGTCTCTCTCCCTGGACATTTCTGAAGGGAAGGTGGAGGCAGCGTGGAGGGGCACCAGGAGCAGGAGTTTCTTGTGTGAGCACCTGTGGGATGC TCTACCCTATATCAGCTATTTGCTCTTTTTCCCTGCACTCCTGGGAGGCTCCCTGTGTTCCTTTCAGAGA TTTCAGGCTTGCGTTCAAAGACCAAGGTCTTTGTATCCAGTATCTCTTTTCGGGCTCTGACCTGGAGGGGTCTGCAGATCCTTGGGCTGGAGTGCCTCAAGGTGGCGCTGAGGAGGGTGGTGAGTGCTGGCGCTGGACT GGATGATTGCCAGCGACTGGAGTGCATCTACATCATGTGGTCCACCGCTGGGCTCTTTAAACTCACCTAC TACTCCCACTGGATCCTGGACGACTCTCTCCTTCACGCGGCGGGCTTTGGATCTGAGGCTGGCCAGAGGC CTGGAGAGGAGAGATACGTCCCGGATGTGGACATTTGGACATTGGAAACTACCCACAGGATCTCCCTGTT CGCGAGGCAGTGGAACCGAAGCACAGCTCAGTGGCTCAAGAGGCOTGTCCTCCAGAGGAGCCGGCGCTGG CCCGTGCTGCAGACTTTTGCCTTCTCTGCCTGGTGGCACGGACTCCACCCAGGACAGGTGTTTGGCTTCC TGTGCTGGTCTGTGATGGTGAAAGCCGACTATCTGATCCACACTTTTGCCAATGGATGTATCAGATCCTG GCCCCTGCGGCTGCTTTATAGATCCCTCACTTGGGCCCACACTCAGATCATCATTGCTTACGTAATGCTG GCCGTGGAGGGCCGGAGCTTTTCCTCTCTCTGCCGGCTGTGCTGTTCTTACAACAGTATCTTCCCTGTAA CGTACTGCCTTTTGCTTTTTCTATTAGCGAGGAGAAAACACAAGTGTAACTGA (SEQ TD NO:05)

Protein Sequence region that we predict on the basis of genomic DNA (corresponding to the first two coding exons in mouse sequence), but absent from the NCBI protein sequence is highlighted with underline;

MDWLQFFFLHPVSLYQGAAFPFALLFNYLCITESFPTRARYLFLLAGGGVLALAAMGPYA
LLIFIPALCAVAMISSLSPQEVHGLTFFFQMGWQTLCHLGLHYKEYYLCEPPPVRFYITL
SSLMLLTQRVTSLSLDISEGKVEAAWRGTRSRSSLCEHLWDALPYISYLLFFPALLGGSL
CSFQRFQACVQRPRSLYPSISFWALTWRGLQILGLECLKVALRRVVSAGAGLDDCQRLEC
IYIMWSTAGLFKLTYYSHWILDDSLLHAAGFGSEAGQRPGEERYVPDVDIWTLETTHRIS
LFARQWNRSTAQWLKRLVFQRSRRWPVLQTFAFSAWWHGLHPGQVFGFLCWSVMVKADYL
IHTFANGCIRSWPLRLLYRSLTWAHTQIIIAYVMLAVEGRSFSSLCRLCCSYNSIFPVTY
CLLLFLLARRKHKCN(SEQ ID NO: 06)

```
atggattggctccagttcttctttctccatcctgtatcactttatcaaggggctgctttc
 M   D   W   L   Q   F   F   F   L   H   P   V   S   L   Y   Q   G   A   A   F cccttcgcgcttctgtttaattatctctgcatcacggaatcctttcccacccgggccagg
 P   F   A   L   L   F   N   Y   L   C   I   T   E   S   F   P   T   R   A   R tacctctttctcctggctggaggaggtgtcctggctttggccgccatgggtccctacgct
 Y   L   F   L   L   A   G   G   G   V   L   A   L   A   A   M   G   P   Y   A ctgctcattttcatccctgctctctgtgccgtggctatgatctcctccctcagtccacag
 L   L   I   F   I   P   A   L   C   A   V   A   M   I   S   S   L   S   P   Q gaagtccatgggctgactttcttctttcagatgggttggcaaaccctgtgccacctgggt
 E   V   H   G   L   T   F   F   F   Q   M   G   W   Q   T   L   C   H   L   G cttcactacaaggagtactacctgtgtgagcctcccctgtgaggttctacatcactctt
 L   H   Y   K   E   Y   Y   L   C   E   P   P   P   V   R   F   Y   I   T   L tcttccctcatgctcttgacgcagagagtcacgtctctctccctggacatttctgaaggg
 S   S   L   M   L   L   T   Q   R   V   T   S   L   S   L   D   I   S   E   G aaggtggaggcagcgtggaggggcaccaggagcaggagttctttgtgtgagcacctgtgg
 K   V   E   A   A   W   R   G   T   R   S   R   S   S   L   C   E   H   L   W
```

-continued

```
gatgctctaccctatatcagctatttgctcttttccctgcactcctgggaggctccctg
```
D   A   L   P   Y   I   S   Y   L   L   F   F   P   A   L   L   G   G   S   L

```
tgttcctttcagagatttcaggcttgcgttcaaagaccaaggtctttgtatcccagtatc
```
C   S   F   Q   R   F   Q   A   C   V   Q   R   P   R   S   L   Y   P   S   I

```
tctttctgggctctgacctggaggggtctgcagatccttgggctggagtgcctcaaggtg
```
S   F   W   A   L   T   W   R   G   L   Q   I   L   G   L   E   C   L   K   V

```
gcgctgaggagggtggtgagtgctggcgctggactggatgattgcagcgactggagtgc
```
A   L   R   R   V   V   S   A   G   A   G   L   D   D   C   Q   R   L   E   C

```
atctacatcatgtggtccaccgctgggctctttaaactcacctactactcccactggatc
```
I   Y   I   M   W   S   T   A   G   L   F   K   L   T   Y   Y   S   H   W   I

```
ctggacgactctctccttcacgcggcgggctttggatctgaggctggccagaggcctgga
```
L   D   D   S   L   L   H   A   A   G   F   G   S   E   A   G   Q   R   P   G

```
gaggagagatacgtcccggatgtggacatttggacattggaaactacccacaggatctcc
```
E   E   R   Y   V   P   D   V   D   I   W   T   L   E   T   T   H   R   I   S

```
ctgttcgcgaggcagtggaaccgaagcacagctcagtggctcaagaggcttgtcttccag
```
L   F   A   R   Q   W   N   R   S   T   A   Q   W   L   K   R   L   V   F   Q

```
aggagccggcgctggcccgtgctgcagacttttgccttctctgcctggtggcacggactc
```
R   S   R   R   W   P   V   L   Q   T   F   A   F   S   A   W   W   H   G   L

```
cacccaggacaggtgtttggcttcctgtgctggtctgtgatggtgaaagccgactatctg
```
H   P   G   Q   V   F   G   F   L   C   W   S   V   M   V   K   A   D   Y   L

```
atccacacttttgccaatggatgtatcagatcctggcccctgcggctgctttatagatcc
```
I   H   T   F   A   N   G   C   I   R   S   W   P   L   R   L   L   Y   R   S

```
ctcacttgggcccacactcagatcatcattgcttacgtaatgctggccgtggagggccgg
```
L   T   W   A   H   T   Q   I   I   I   A   Y   V   M   L   A   V   E   G   R

```
agcttttcctctctctgccggctgtgctgttcttacaacagtatcttccctgtaacgtac
```
S   F   S   S   L   C   R   L   C   C   S   Y   N   S   I   F   P   V   T   Y

```
Tgccttttgcttttctattagcgaggagaaaacacaagtgtaactga (SEQ ID NO:07)
```
C   L   L   L   F   L   L   A   R   R   K   H   K   C   N   -   (SEQ ID NO:06)

Human

[The predicted cDNA sequence for human GOAT, shown below, was verified experimentally by reverse transcription/polymerase chain reaction (RT PCR) of human stomach RNA (obtained from Clontech), followed by cDNA cloning in *E. coli* of the RT PCR product (inserted into pcDNA3 vector) and DNA sequencing of the cloned cDNA. This sequence verification was performed on Dec. 20, 2007.]

Coding DNA Region in 3 Exons

>ref |NT_007995.14 |Hs8_8152:c322891-322772 *Homo sapiens* chromosome 8 genomic contig, reference assembly ATGGAGTGGCTTTGGCTGTTCTTTCTC-CATCCTATATCGTTTTACCAGGGGGCTG-CATTTCCCTTTGCAC TTCTCTTCAATTATCTCTGCAT-CATGGATTCATTCTCCACTCGTGCCAGG (SEQ ID NO:08)>

>ref |NT_007995.14 |Hs8_8152:c317045-316821 *Homo sapiens* chromosome 8 genomic contig, reference assembly TACCTCTTTCTCCTGACTGGAGGAGGT-GCCCTGGCCGTGGCTGCCATGGGTTC-CTACGCCGTGCTCGTCT TCACCCCTGCTGTCT-GCGCTGTGGCTCTCCTCTGTTCCCTGGCTCCTCAG-CAAGTCCACAGGTGGACCTT CTGCTTOCAGAT-GAGCTGGCAGACCTTGTGTCACCTAG-GTCTGCACTACACTGAGTATTATTCGCATGAG CCTC-CTTTCGTGAGG (SEQ ID NO:09)

>ref |NT_007995.14 |Hs8_8152:c311195-310233 *Homo sapiens* chromosome 8 genomic contig, reference assembly TTCTGCATCACTCTTTTTTTTCTCATGCTCTTGA-CCCAGAGGGTCACGTCCCTCTTTCTGGACATTTGT-G AGGGGAAAGTGAAGGCAGCATTCGGAGGCTTC-AGGAGCAGGAGCTTTTTGTCTGAGCAT-GTGTGTAAGGC ACTGCCCTATTTCAGCTACT-TGCTCTTTTTCCCTGCTCTCCTGGGAG- GCTTTCTGTGCTCCTTCCAGCGA TTTCAGGCTCGT-
GTTCAAGGGTCCAGTGCTTTGCATCCCAGACACTC-
TTCCTGGGCTTCGAGCTGGAGGG GTCTGCAGAT-
TCTTGGACTAGAATGCCTAAACGTGGCAGTGA-
GCAGGGTGGTGGATGCAGGAGCGGGACT GACT-
GATTGCCAGCAATTCGAGTGCATCTATGTCGTG-
TGGACCACAGCTGGGCTTTTCAAGCTCACCTAC
TACTCCCACTGGATCCTGGACGACTC-
CCTCCTCCACGCAGCGGGCTTTGGGCCT-
GAGCTTGGTCAGAGCC CTGGAGAGGAGGGATAT-
GTCCCCGATGCAGACATCTGGACCCTGGAAAGAAC-
CCACAGGATATCTGTGTT CTCAAGAAAGTGGAAC-
CAAAGCACAGCTCGATGGCTCCGACG-
GCTTGTATTCCAGCACAGCAGGGCTTGG CCGTTGT-
TGCAGACAATTTGCCTTTCTCGTCCTGGGGCAGGA-
CTCCATCCAGGACAGGGTTTTGGTTTCG TTTGCTGGGCCGTGAAGGTGGAAGCT-
GACTACCTGATTCACTCCTTTGCCAAT-
GATTTATACAGATCCTG GCCGATGAGGCTGTTCTT-
TAGAACCCTCACCTGGGCCCACACCCAGTTGATCA-
TTGCCTACATATCAGCG GCTGTGGAGGTCAG-
GAGTCTTCTTTTTTTCCTTGTCT-
TGTCTAATTCGTACAACAGGTCTTTTCCCATGG
TGTACTGTATTCTGCTTTTGCTATTGGC-
GAAGAGAAAGCACAAATGTAACTGA (SEQ ID
NO:010)

Protein Sequence region that we predict on the basis of genomic DNA (corresponding to the first two coding exons in mouse sequence), but absent from the NCBI protein sequence is highlighted in underline;

<u>MEWLFFLHPISFYQGAAFPFALLFNYLCIMDSFSTRARYLFLLTGGGALAVAAMGSYA</u>
<u>VLVFTPAVCAVLLCSLAPQQVHRWTFCFQMSWQTLCHLGLHYTEYYLHEPPSV</u>RFCITL
SSLMLLTQRVTSLSLDICEGKVKAASGGFRSRSSLSEHVCKALPYFSYLLFFPALLGGSL
CSFQRFQARVQGSSALHPRHSFWALSWRGLQILGLECLNVAVSRVVDAGAGLTDCQQFEC
IYVVWTTAGLFKLTYYSHWILDDSLLHAAGFGPELGQSPGEEGYVPDADIWTLERTHRIS
VFSRKWNQSTARWLRRLVFQHSRAWPILQTAFAFSAWWHGKHPGQVFGVCWAVMVEADYL
IHSFANEFIRSWPMRLFYRTLTWAHTQLIIAYIMLAVEVRSLSSLWLLCYSYNSVFPMVY
CILLLLLAKRKEKCN(SEQ ID NO:11)

```
atggagtggctttggctgttctttctccatcctatatcgttttaccaggggggctgcattt
 M   E   W   L   F   F   L   H   P   I   S   F   Y   Q   G   A   A   F
cctttgcacttctcttcaattatctctgcatcatggattcattctccactcgtgccagg
 P   F   A   L   L   F   N   Y   L   C   I   M   D   S   F   S   T   R   A   R
tacctctttctcctgactggaggaggtgccctggccgtggctgccatgggttcctacgcc
 Y   L   F   L   L   T   G   G   G   A   L   A   V   A   A   M   G   S   Y   A
gtgctcgtcttcacccctgctgtctgcgctgtggctctcctctgttccctggctcctcag
 V   L   V   F   T   P   A   V   C   A   V   L   L   C   S   L   A   P   Q
caagtccacaggtggaccttctgctttcagatgagctggcagaccttgtgtcacctaggt
 Q   V   H   R   W   T   F   C   F   Q   M   S   W   Q   T   L   C   H   L   G
ctgcactacactgagtattatctgcatgagcctccttctgtgaggttctgcatcactctt
 L   H   Y   T   E   Y   Y   L   H   E   P   P   S   V   R   F   C   I   T   L
tcttctctcatgctcttgacccagagggtcacgtccctctctctggacatttgtgagggg
 S   S   L   M   L   L   T   Q   R   V   T   S   L   S   L   D   I   C   E   G
aaagtgaaggcagcatctggaggcttcaggagcaggagctcttttgtctgagcatgtgtgt
 K   V   K   A   A   S   G   G   F   R   S   R   S   S   L   S   E   H   V   C
aaggcactgccctatttcagctacttgctcttttttccctgctctcctgggaggctctctg
 K   A   L   P   Y   F   S   Y   L   L   F   F   P   A   L   L   G   G   S   L
tgctccttccagcgatttcaggctcgtgttcaagggtccagtgctttgcatcccagacac
 C   S   F   Q   R   F   Q   A   R   V   Q   G   S   S   A   L   H   P   R   H
tcttttctgggctctgagctggaggggtctgcagattcttggactagaatgcctaaacgtg
```

-continued

```
  S  F  W  A  L  S  W  R  G  L  Q  I  L  G  L  E  C  L  N  V
gcagtgagcagggtggtggatgcaggagcgggactgactgattgccagcaattcgagtgc A  V  S  R  V  V  D  A  G  A  G  L  T  D  C  Q  Q  F  E  C
atctatgtcgtgtggaccacagctgggcttttcaagctcacctactactcccactggatc I  Y  V  V  W  T  T  A  G  L  F  K  L  T  Y  Y  S  H  W  I
ctggacgactccctcctccacgcagcgggctttgggcctgagcttggtcagagccctgga L  D  D  S  L  L  H  A  A  G  F  G  P  E  L  G  Q  S  P  G
gaggagggatatgtccccgatgcagacatctggaccctggaaagaacccacaggatatct E  E  G  Y  V  P  D  A  D  I  W  T  L  E  R  T  H  R  I  S
gtgttctcaagaaagtggaaccaaagcacagctcgatggctccgacggcttgtattccag V  F  S  R  K  W  N  Q  S  T  A  R  W  L  R  R  L  V  F  Q
cacagcagggcttggccgttgttgcagacatttgccttctctgcctggtggcatggactc H  S  R  A  W  P  L  L  Q  T  F  A  F  S  A  W  W  H  G  L
catccaggacaggtgtttggtttcgtttgctgggccgtgatggtggaagctgactacctg H  P  G  Q  V  F  G  F  V  C  W  A  V  M  V  E  A  D  Y  L
attcactcctttgccaatgagtttatcagatcctggccgatgaggctgttctatagaacc I  H  S  F  A  N  E  F  I  R  S  W  P  M  R  L  F  Y  R  T
ctcacctgggcccacacccagttgatcattgcctacatcatgctggctgtggaggtcagg L  T  W  A  H  T  Q  L  I  I  A  Y  I  M  L  A  V  E  V  R
agtctctcctctctctggttgctctgtaattcgtacaacagtgtctttcccatggtgtac S  L  S  S  L  W  L  L  C  N  S  Y  N  S  V  F  P  M  V  Y
Tgtattctgcttttgctattggcgaagagaaagcacaaatgtaactga  (SEQ ID NO:12)

C  I  L  L  L  L  L  A  K  R  K  H  K  C  N  -  (SEQ ID NO:11)
```

Chimpanzee

Correct protein sequence is present in the database

>gi |114619777 ref |XP_519692.2 |PREDICTED: hypothetical protein LOC464094 [Pan troglodytes]

MEWLRLFFLHPVSFYQGAAFPFALLF-
NYLCIMDSFSTRARYLFLLAGGGALA-
VAAMGSYAVLVFIPAVCA VALLCSLAPQQVHR-
WIFCFQMSWQTLCHLGLHYTEYYLHEPPSVRFCITL-
SSLMLLIQRVISLSLDICEG KVEAASGGFRSRSSLSEH-
VCKALPYFSYLLFFPALLGGSLCSFQR-
FQARVQGSSALHPRHSFWALSWRCL QILGLECLN-
VAVSRVVDAGAGLTDCQQFECIYVVWITAGLFKLTY-
YSHWILDDSLLHAAGFGPELGQSPG EEGYVPDADI-
WILERTHRISVFARKWNQSTARWLRRLVFQHSR-
AWPLLQTFAFSAWWHGLHPGQVFGFVC WAVMVE-
ADYLIHSFANEFIRSWPMRLFYRTLIWAHIQLI-
IAYIMLAVEVRSLSSLWLLCNSYNSVFPMVY CIL-
LLLLVKRKHKCN (SEQ ID NO:13)

Bovine

Coding DNA Region in 3 Exons

>ref |NW_001494415.1 |Bt27_WGA2723_3:c220739-
220620 Bos taurus chromosome 27 genomic contig, reference assembly (based on Btau_3.1), whole genome shotgun sequence ATGGATTGGCTCCAGCTGTTTTCCTTTGATCC-
TGTATCACTTTATCAAGGAGCTGCTTTC-
CCTTTTGCAC TTCTGTTTAATCATTTCTGTGTTATG-
GATTCATTTTCCACTCAGGCCAGG (SEQ ID NO:14)

>ref |NW_001494415.1 |Bt27_WGA2723_3:c216688-
216464 Bos taurus chromosome 27 genomic contig, reference assembly (based on Btau_3.1), whole genome shotgun sequence TACCTGTTCCTCCTGGCGGGAGGCGGT-
GCCCTGGCCGTGGCTGCTATGGGTGCCT-
TCGCTGTGCTGGTTC TCATCCCCGCCCTGTGCACG-
GTGGTCCTTATCCACTCGCTTGGCCCCCAGGATGT-
CCACAGGCCGACCTT CCTTTTTCAGATGACCTG-
GCAGACGCTGTGCCACCTGGGTCTGCAC-
TATACGGAGTATTATTCGCAAGAA GCTCCTTCTA-
CAAGG (SEQ ID NO:15)

>|ref |NW_001494415.1 |Bt27_WGA2723_3:c212687-
211725 Bos taurus chromosome 27 genomic contig, reference assembly (based on Btau_3.1), whole genome shotgun sequence TTCTGCATTCACTTCTTCTCGCTCAT-
GCTCTTGACCCAGAAGATCACATTTCT-
GTTCTCGGATATTCGTG AGGGGAAGGTGGTAGCAC-
CATCAGGACGCATCCCTAACAAGAATTTTTTGTCTG-
AGCATTCGCATGCGGC TCTTCCCTATCTCAGCTACT- TGCTCTTCTTCCCTGCCCTCCTAGGAG-
GCCCGCTGTGTTCCTTCCAGAGG TTTCAGGCTC-
GAGTTGAAGGGTCCAGCAGTTTGTGGTCCAGGCAC-
TCTTCCTGGGCTTCGACCTGGAGGG CGCTGCA-
GATCCTGGGACTGGAGAGTCTGAAGGTGATCGTC-
AGCGGGGTGGTGGGCGTGGGGGCAGGACT
TGGAGGCTGCAGGCAGCTGCAGT-
GCGTCTTCGTCCTGTGGTCCACGGC-
CGGGCTCTTCAAACTCACCTAC TACTCCCACTG-
GCTCCTGGATGACGCCCTCCTCCGCGCGGCCGGCT-
TTGGATTCGAGTTAGGTCGCAGCC CGGGTGAG-
GAGGGACTCCTCCCCGATGCGGACATTTGG-
ACGCTGGAAACGACCCACAGGATAGCCCTGTT
CGCCAGGAAGTGGAACCAGAGCACG-
GCTCGGTGGCTCCGACGCCTGGTTTTC-
CAGCAGCGCAGGACCTGG CCCTTGTTGCAGACAT-
TCCCTTTTTCGGCCTGGTGGCACGGTTCCCACCCG-
GGACAGGTGTTTGGTTTCC TCTCGTGGGCTGT-
CATGGTGGAAGCCGACTACCTGAT-
TCACGCCTTCGCCAGCGTGTTCATCAGCTCCTG
GCCCATGCGGCTGCTCTACAGAGCCCTG-
GCCTGGGCCCACACCCAGCTCAT-
CATCGCCTACATAATGCTG GCCGTGGAGGCCCG-
GAGCCTTTCCTTTCTTCGGCTGCTGTGGAATTCTTA-
CAGCAGTGTCTTTCCCACGG TGTACTGTATTTTGCT-
TCTCCTGTTAGCAAAGAGAAAGCAT-
AAATGCAACTGA (SEQ ID NO:16)

Protein Sequence region that we predict on the basis of genomic DNA (corresponding to the first two coding exons in mouse sequence), but absent from the NCBI protein sequence is highlighted in underline;

<u>MDWLQLFFLDPVSLYQGAAFPFALLFNHLCVMDSFSTQARTLFLLAGGGALAVAAMGAFA</u>
<u>VLVFIPALCTVVLIHSLGPQDVHRPTFLFQMTWQTLCHLGLHYTEYYLQEAPST</u>RFCITL
SSLMLLTQKITSLSLDIREGKVVAPSGRIPNKNSLSEHLHAALPYLSYLLFFPALLGGPL
CSFQRFQARVEGSSSLWSRHSFWALTWRALQILGLESLKVIVSGVVGVGAGLGGCRQLQC
VFVLWSTAGLFKLTYYSHWLLDDALLRAAGFGSELGRSPGEEGLLPDADIWTLETTHRIA
LFARKWNQSTARWLRRLVFQQRRTWPLLQTFLFSAWWHGLHPGQVFGFLCWAVMVEADYL
IHAFASVFISSWPMRLLYRALAWAHTQLIIAYIMLAVEARSLSSLWLLWNSYSSVFPTVY
CILLLLLAKRKHKCN- (SEQ ID NO:17)

```
atggattggctccagctgttcttccttgatcctgtatcactttatcaaggagctgctttt
 M   D   W   L   Q   L   F   F   L   D   P   V   S   L   Y   Q   G   A   A   F ccttttgcacttctgtttaatcatctctgtgttatggattcattttccactcaggccagg
 P   F   A   L   L   F   N   H   L   C   V   M   D   S   F   S   T   Q   A   R tacctgttcctcctggcgggaggcggtgccctggccgtggctgctatgggtgccttcgct
 Y   L   F   L   L   A   G   G   G   A   L   A   V   A   A   M   G   A   F   A gtgctggtcttcatccccgccctgtgcacggtggtcctcatccactcgcttggccccag
 V   L   V   F   I   P   A   L   C   T   V   V   L   I   H   S   L   G   P   Q gatgtccacaggccgaccttcctctttcagatgacctggcagacgctgtgccacctggt
 D   V   H   R   P   T   F   L   F   Q   M   T   W   Q   T   L   C   H   L   G ctgcactatacggagtattatctgcaagaagctccttctacaaggttctgcatcactctc
 L   H   Y   T   E   Y   Y   L   Q   E   A   P   S   T   R   F   C   I   T   L tcttcgctcatgctcttgacccagaagatcacatctctgtctctggatattcgtgagggg
 S   S   L   M   L   L   T   Q   K   I   T   S   L   S   L   D   I   R   E   G aaggtggtagcaccatcaggacgcatccctaacaagaattctttgtctgagcatctgcat
 K   V   V   A   P   S   G   R   I   P   N   K   N   S   L   S   E   H   L   H gcggctcttccctatctcagctacttgctcttcttccctgccctcctaggaggcccgctg
 A   A   L   P   Y   L   S   Y   L   L   F   F   P   A   L   L   G   G   P   L tgttccttccagaggtttcaggctcgagttgaagggtccagcagtttgtggtccaggcac
 C   S   F   Q   R   F   Q   A   R   V   E   G   S   S   S   L   W   S   R   H
```

-continued

```
tctttctgggctctgacctggagggcgctgcagatcctgggactggagagtctgaaggtg
 S  F  W  A  L  T  W  R  A  L  Q  I  L  G  L  E  S  L  K  V
atcgtcagcggggtggtgggcgtgggggcaggacttggaggctgcaggcagctgcagtgc
 I  V  S  G  V  V  G  V  G  A  G  L  G  G  C  R  Q  L  Q  C
gtcttcgtcctgtggtccacggccgggctcttcaaactcacctactactcccactggctc
 V  F  V  L  W  S  T  A  G  L  F  K  L  T  Y  Y  S  H  W  L
ctggatgacgccctcctccgcgcggccggctttggatctgagttaggtcgcagcccgggt
 L  D  D  A  L  L  R  A  A  G  F  G  S  E  L  G  R  S  P  G
gaggagggactcctccccgatgcggacatttggacgctggaaacgacccacaggatagcc
 E  E  G  L  L  P  D  A  D  I  W  T  L  E  T  T  H  R  I  A
ctgttcgccaggaagtggaaccagagcacggctcggtggctccgacgcctggttttccag
 L  F  A  R  K  W  N  Q  S  T  A  R  W  L  R  R  L  V  F  Q
cagcgcaggacctggcccttgttgcagacattcctcttctcggcctggtggcacggtctc
 Q  R  R  T  W  P  L  L  Q  T  F  L  F  S  A  W  W  H  G  L
cacccgggacaggtgtttggtttcctctgctgggctgtcatggtggaagccgactacctg
 H  P  G  Q  V  F  G  F  L  C  W  A  V  M  V  E  A  D  Y  L
attcacgccttcgccagcgtgttcatcagctcctggcccatgcggctgctctacagagcc
 I  H  A  F  A  S  V  F  I  S  S  W  P  M  R  L  L  Y  R  A
ctggcctgggcccacacccagctcatcatcgcctacataatgctggccgtggaggcccgg
 L  A  W  A  H  T  Q  L  I  I  A  Y  I  M  L  A  V  E  A  R
agcctctcctctctctggctgctgtggaattcttacagcagtgtctttcccacggtgtac
 S  L  S  S  L  W  L  L  W  N  S  Y  S  S  V  F  P  T  V  Y
Tgtattttgcttctcctgttagcaaagagaaagcataaatgcaactga (SEQ ID NO:18)
 C  I  L  L  L  L  A  K  R  K  H  K  C  N  -  (SEQ ID NO:17)
```

Horse

Coding DNA Region in 3 Exons

>ref |NW_001799700.1| |Eca27_WGA83_1:7589091-7589210 *Equus caballus* chromosome 27 genomic contig, reference assembly (based on EquCab1 scaffold_68), whole genome shotgun sequence ATGGGTTGGCTTCAGCTGTTCCTTCTCCATCCTGTATCACTTTATCAAGGGGCCGCTTTTCCTTTTGCAC TTCTATTTAATTACCTTTGCACTATGGATTCATTTTCCACTCATGCCAGG (SEQ ID NO:19)

>ref |NW_001799700.1| |Eca27_WGA83_1:7591734-7591958 *Equus caballus* chromosome 27 genomic contig, reference assembly (based on EquCab1 scaffold_68), whole genome shotgun sequence TACCTCTTTCTGCTGGCAGGAGGAGGCGCCCTGGCCTTGGCCGCTATGGGTCCCTTTGCTGTGCTTGTCT TCATCCCTGCGATATGTGCTGTGTTTCTGATCTGCTTGCTCAGCCCACAGGArAGTCCACAGGCAGACTTTCTGCTTTCAGATGAGCTGGCAGACGCTGTGTCACCTGGGTCTGCACTATACTGAGTATTATCTGCAAGAA CTTCCTTCCACGAGG (SEQ ID NO:20)

>ref |NW_001799700.1| Eca27_WGA83_1:7594135-7595097 *Equus caballus* chromosome 27 genomic contig, reference assembly (based on EquCab1 scaffold_68), whole genome shotgun sequence TTCTGCCTCGCTTTTCTTCCCTCATGCTTCTTGACCCAGAGGGTCACATTCCCTTCTTCGGACATTTGTG AAGGGAAACTGGCAGCAGCATCAGGAGGCACCAGGAGCAGAAGCTTTCTTGTCrGAGCATTCGTGTAAGGC ACTGCCCTATTTCAGCTACTTGCTTTTTTTTCCTGCTCTCCTAGGAGGCCCCTTGTGTTCCTTCCAGAGA TTTCAGGCCCGTGTTCAAGGGCCCAGCAACTTGTGTCCCAGGCACCCTTTCAGGGCTTCGACCTGGAGGG GTCTGCAGATTTCGGGACTAGAGTGCCTAAAGGTCGTCATGAGGGCAGTGGTGAGAGCAGGAGCAGGACT GACCGACTGCCGGCAACTCCAGTGCATCTATGTCATGTGGTCCACAGCCGGGCTTTTCAAACTCACCTAC TACTCCCACTGGATCCTGGATGACTCCCTCCTGTGTGCAGCGGGCTT TGGATTCGAGTTTGGGCAGAGCC CTGGTGAG-
GACGGATACATTCCCGATGCAGA-
CATTTGGACACTGGAAACAACCCACAG-
GATATTCCCGTT
TGCGAGAAAGTGGAACCAAAGCA-
CAGCTCGGTGGCTCAGACGCCTCG-
TATTTCAGCACAGCAGGGTCTGG CCGTTGTTGCA-
GACATTTGCATTTTCTGCCTGGTGGCATGGGCTCCA-
TCCAGGACAGGTGTTTGGTTTCC CTTGCTGGGCT-
GTGATGGTGGAAGCTGACTACCTGAT-
TCACACCTTTGCCAAATTGTTTATCAGATCCTG
GCCGATGAAGCTGCTCTATAGAACTTC-
GACCTGGGCCCACACCCAGCTCATCATT-
GCCTACATAATGCTG GCCGTGGAGGTCAGGAGC-
CTCTCCTCTCTCTGGCTGCTGTGTAAT-
TCTTACAACAGTGTCTTTCCCAGG TGTATTG-
TATTTTGCTTTTGCTATTAGCAAAGAGAAAGCACAC-
ATTTAACTGA (SEQ ID NO:21)

Protein Sequence region that we predict on the basis of genomic DNA (corresponding to the first two coding exons in mouse sequence), but absent from the NCBI protein sequence is highlighted in underline;

<u>MGWLQLFLLHPVSLYQGAAFPFALLFNYLCTMDSFSTHARYLFLLAGGGALALAAMGPFA</u>
<u>VLVFIPAICAVFLICLLSPQEVHRQTFCFQMSWQTLCHLGLHYTEYYLQELPST</u>RFCLAL

SSLMLLTQRVTSLSLDICEGKLAAASGGTRSRSSLSEHLCKALPYFSYLLFFPALLGGPL

CSFQRFQARVQGPSNLCPRHPFRALTWRGLQILGLECLKVVMRAVVRAGAGLTDCRQLQC

IYVMWSTAGLFKLTYYSHWILDDSILCAAGFGSEFGQSPGEDGYIPDADIWTLETTHRIS

LFARKWNQSTARWLRRLVFQHSRVWPLLQTFAFSAWWHGLHPGQVFGFLCWAVMVEADYL

IHTFAKLFIRSWPMKLLYRTLTWAHTQLIIAYIMLAVEVRSLSSLWLLCNSYNSVFPMVY

CILLLLLAKRKHTFN(SEQ ID NO: 22)

```
atgggttggcttcagctgttccttctccatcctgtatcactttatcaaggggccgctttt
 M   G   W   L   Q   L   F   L   L   H   P   V   S   L   Y   Q   G   A   A   F ccttttgcacttctatttaattacctttgcactatggattcattttccactcatgccagg
 P   F   A   L   L   F   N   Y   L   C   T   M   D   S   F   S   T   H   A   R tacctctttctgctggcaggaggaggcgccctggccttggccgctatgggtcccttgct
 Y   L   F   L   L   A   G   G   G   A   L   A   L   A   A   M   G   P   F   A gtgcttgtcttcatccctgcgatatgtgctgtgtttctgatctgcttgctcagcccacag
 V   L   V   F   I   P   A   I   C   A   V   F   L   I   C   L   L   S   P   Q gaagtccacaggcagactttctgctttcagatgagctggcagacgctgtgtcacctgggt
 E   V   H   R   Q   T   F   C   F   Q   M   S   W   Q   T   L   C   H   L   G ctgcactatactgagtattatctgcaagaacttccttccacgaggttctgcctcgctctt
 L   H   Y   T   E   Y   Y   L   Q   E   L   P   S   T   R   F   C   L   A   L tcttccctcatgctcttgacccagagggtcacatccctctctctggacatttgtgaaggg
 S   S   L   M   L   L   T   Q   R   V   T   S   L   S   L   D   I   C   E   G aaactggcagcagcatcaggaggcaccaggagcagaagctctttgtctgagcatctgtgt
 K   L   A   A   A   S   G   G   T   R   S   R   S   S   L   S   E   H   L   C aaggcactgccctatttcagctacttgcttttttttcctgctctcctaggaggccctctg
 K   A   L   P   Y   F   S   Y   L   L   F   F   P   A   L   L   G   G   P   L tgttccttccagagatttcaggcccgtgttcaagggcccagcaacttgtgtcccaggcac
 C   S   F   Q   R   F   Q   A   R   V   Q   G   P   S   N   L   C   P   R   H cctttcagggctctgacctggaggggtctgcagattctgggactagagtgcctaaaggtc
 P   F   R   A   L   T   W   R   G   L   Q   I   L   G   L   E   C   L   K   V gtcatgagggcagtggtgagagcaggagcaggactgaccgactgccggcaactccagtgc
```

-continued

```
V  M  R  A  V  V  R  A  G  A  G  L  T  D  C  R  Q  L  Q  C
atctatgtcatgtggtccacagccgggctcttcaaactcacctactactcccactggatc I  Y  V  M  W  S  T  A  G  L  F  K  L  T  Y  Y  S  H  W  I
ctggatgactccctcctgtgtgcagcgggctttggatctgagtttgggcagagccctggt L  D  D  S  L  L  C  A  A  G  F  G  S  E  F  G  Q  S  P  G
gaggacggatacatccctgatgcagacatttggacactggaaacaacccacaggatatcc E  D  G  Y  I  P  D  A  D  I  W  T  L  E  T  T  H  R  I  S
ctgtttgcgagaaagtggaaccaaagcacagctcggtggctcagacgcctcgtatttcag L  F  A  R  K  W  N  Q  S  T  A  R  W  L  R  R  L  V  F  Q
cacagcagggtctggccgttgttgcagacatttgcattctctgcctggtggcatgggctc H  S  R  V  W  P  L  L  Q  T  F  A  F  S  A  W  W  H  G  L
catccaggacaggtgtttggtttcctctgctgggctgtgatggtggaagctgactacctg H  P  G  Q  V  F  G  F  L  C  W  A  V  M  V  E  A  D  Y  L
attcacacctttgccaaattgtttatcagatcctggccgatgaagctgctctatagaact I  H  T  F  A  K  L  F  I  R  S  W  P  M  K  L  L  Y  R  T
ctgacctgggcccacacccagctcatcattgcctataatgctggccgtggaggtcagg L  T  W  A  H  T  Q  L  I  I  A  Y  I  M  L  A  V  E  V  R
agcctctcctctctctggctgctgtgtaattcttacaacagtgtctttcccatggtgtat S  L  S  S  L  W  L  L  C  N  S  Y  N  S  V  F  P  M  V  Y
Tgtattttgcttttgctattagcaaagagaaagcacacatttaactga (SEQ ID NO:23)

C  I  L  L  L  L  A  K  R  K  H  T  F  N  -  (SEQ ID NO:22)
```

Zebrafish

Coding DNA Region in 3 Exons

>ref |NW_001513480.1 |Dr5_WGA761_2:794788-794913 Danio rerio chromosome 5 genomic contig, reference assembly (based on Zv6_scaffold 761:1-1770220)

ATGATAGATCTCCTTTGGATTTCTTCT-GATGGACACCCTCAGCTGTTTTAC-CAGTTTATCAACATACCAT TTGCATTTCTGTTTCAT-TGCTTATCCAGTCAAGGACATCTCTCGATAATCAAC-AGG (SEQ ID NO:24)

>ref |NW_001513480.1 |Dr5_WGA761_2:794996-795220 Danio rerio chromosome 5 genomic contig, reference assembly (based on Zv6_scaffold 761:1-1770220)
TACGTCTATTTGGCGATGGGAGGAT-TCATGCTGGCTATTGCAACAATGGGTC-CATATAGCTCACTGCTGT TCCTGAGTGCTAT-TAAACTGCTGTTACTGATCCACTATATACATCCAATG-CATCTTCATCGGTGGATTCT GGGACTGCAGATGT-GTTGGCAAACCTGCTGGCATTTG-TACGTCCAGTACCAGATATACTGGCTTCAAGAG GCACCAGACTCAAGG (SEQ ID NO:25)

>ref |NW_001513480.1 |Dr5_WGA761_2:797189-798085 Danio rerio chromosome 5 genomic contig, reference assembly (based on Zv6_scaffold 761:1-1770220)
CTTTTACTGGCCATATCTGCACTCATGT-TGATGACCCAGAGGATTTCCTCTCTAT-CACTCGATTTCCAAG AGGGGACGATCTCCAAT-CAGTCAATCCTTATCCCATCCCTAACCTACTCGCTC-TTATTCCCCGCCCTTCT TGGAGGTCCACTTTG-CAGTTTCAATGCTTTTGTTCAGTCTGTC-GAGCGTCAACACACCAGCATGACTTCA TATTTAG-GAAATCTCACTTCAAAGATATCACAAGTTATAGTTT-TGGTGTGGATTAAACAGCTTTTCAGTG AGCTTTTGAAATCTGCCACGTTTAA-CATCGACAGTGTTTGTCTTGATGTAT-TGTGGATTTGGATCTTTTC GCTGACACTTAGGCT-TAATTACTATGCACACTGGAAGATGAGCGAGTGTGT-TAATAATGCTGCAGGATTT GGTGTCTATTTACA-CAAACACAGTGGACAAACATCATGG-GACGGTCTTTCTGATGGGAGTGTACTGGTGA CTGAAGCATCCAGTCGTCCTTCG-GTTTTTGCGCGAAAGTGGAACCAAAC-CACGGTGGATTGGCTTCGAAA AATAGTTCCTAA-CAGGACCAGCAGATTTCCACTGTTCATGACTTTTGG-GTTTTTCGCACTGTGGCACGGT CTTCAC-CCTGGGCAGATTCTGGGTTTC-CCTATTTGGGCCGTCACTGTGCAGGCG-GACTACAAACTGCATC GCTTCTTGCACCCGAAGCTTAACTCCCT-GTGGAGAAAACGGCTGTATGTGTGTG-TAAACTGGGCCTTTAC TCAGCTGACCGTCGCATGT-GTTGTGGTCTGTGTGGAGCTTCAGAGTTTGGCATC-AGTTAAGCTGCTTCGG TTTCCGTGTATTGCTGT-GTTTCCACTGCTGAGTGCTTCGATCT-TAATAATCCTCTGA (SEQ ID NO:26)

Protein Sequence region that we predict on the basis of genomic DNA (corresponding to the first coding exons in mouse sequence), but absent from the NCBI protein sequence is highlighted in underline;

<u>MIDLLWISSDGHPQLFYQFINIPFAFLFHCLSSQGHLSIINRYVYLA</u>MGGFMLAIATMGP
YSSLLFLSAIKLLLLIHYIHPMHLHRWILGLQMCWQTCWHLYVQYQIYWLQEAPDSRLLL
AISALMLMTQRISSLSLDFQEGTISNQSILIPFLTYSLYFPALLGGPLCSFNAFVQSVER
QHTSMTSYLGNLTSKISQVIVLVWIKQLFSELLKSATFNIDSVCLDLWIWIIFSLTLRLN
YYAHWKMSECVNNAAGFGVYLHKHSGQTSWDGLSDGSVLVTEASSRPSVFARKWNQTTVD
WLRKIVFNRTSRSPLFMTFGFSALWHGLHPGQILGFLIWAVTVQADYKLHRFLHPKLNSL
WRKRLYVCVNWAFTQLTVACVVVCVELQSLASVKLLWSSCIAVFPLLSALILIIL (SEQ ID NO: 27)

```
atgatagatctcctttggatttcttctgatggacaccctcagctgttttaccagtttatc
 M   I   D   L   L   W   I   S   S   D   H   P   Q   L   F   Y   Q   F   I
aacataccatttgcatttctgtttcattgcttatccagtcaaggacatctctcgataatc
 N   I   P   A   F   L   F   H   C   L   S   S   Q   G   H   L   S   I   I
aacaggtacgtctatttggcgatggaggattcatgctggctattgcaacaatgggtcca
 N   R   Y   V   Y   L   A   M   G   G   F   M   L   A   I   A   T   M   G   P
tatagctcactgctgttcctgagtgctattaaactgctgttactgatccactatatacat
 Y   S   S   L   L   F   L   S   A   I   K   L   L   L   I   H   Y   I   H
ccaatgcatcttcatcggtggattctgggactgcagatgtgttggcaaacctgctggcat
 P   M   H   L   H   R   W   I   L   G   L   Q   M   C   W   Q   T   C   W   H
ttgtacgtccagtaccagatatactggcttcaagaggcaccagactcaaggcttttactg
 L   Y   V   Q   Y   Q   I   Y   W   L   Q   E   A   P   D   S   R   L   L   L
gccatatctgcactcatgttgatgacccagaggatttcctctctatcactcgatttccaa
 A   I   S   A   L   M   L   M   T   Q   R   I   S   S   L   S   L   D   F   Q
gaggggacgatctccaatcagtcaatccttattccattcctaacctactcgctttatttc
 E   G   T   I   S   N   Q   S   I   L   I   P   F   L   T   Y   S   L   Y   F
cctgccttcttggaggtccactttgcagtttcaatgcttttgttcagtctgtcgagcgt
 P   A   L   L   G   G   P   L   C   S   F   N   A   F   V   Q   S   V   E   R
caacacaccagcatgacttcatatttaggaaatctcacttcaaagatatcaagttata
 Q   H   T   S   M   T   S   Y   L   G   N   L   T   S   K   I   S   Q   V   I
gttttggtgtggattaaacagcttttcagtgagcttttgaaatctgccacgttaacatc
 V   L   V   W   I   K   Q   L   F   S   E   L   L   K   S   A   T   F   N   I
gacagtgtttgtcttgatgtattgtggatttggatcttttcgctgacacttaggcttaat
 D   S   V   C   L   D   V   L   W   I   W   I   F   S   L   T   L   R   L   N
tactatgcacactggaagatgagcgagtgtgttaataatgctgcaggatttggtgtctat
 Y   Y   A   H   W   K   M   S   E   C   V   N   N   A   A   G   F   G   V   Y
ttacacaaacacagtggacaaacatcatgggacggtcttctgatgggagtgtactggtg
 L   H   K   H   S   G   Q   T   S   W   D   G   L   S   D   G   S   V   L   V
```

-continued

```
actgaagcatccagtcgtccttcggttttgcgcgaaagtggaaccaaaccacggtggat
```
T E A S S R P S V F A R K W N Q T T V D

```
tggcttcgaaaaatagtcttcaacaggaccagcagatctccactgttcatgacttttggg
```
W L R K I V F N R T S R S P L F M T F G

```
tttctgcactgtggcacggtcttcaccctgggcagattctgggtttcctcatttgggcc
```
F S A L W H G L H P G Q I L G F L I W A

```
gtcactgtgcaggcggactacaaactgcatcgcttcttgcacccgaagcttaactccctg
```
V T V Q A D Y K L H R F L H P K L N S L

```
tggagaaaacggctgtatgtgtgtgtaaactgggcctttactcagctgaccgtcgcatgt
```
W R K R L Y V C V N W A F T Q L T V A C

```
gttgtggtctgtgtggagcttcagagtttggcatcagttaagctgctctggtcttcgtgt
```
V V V C V E L Q S L A S V K L L W S S C

```
Attgctgtgtttccactgctgagtgctctgatcttaataatcctctga (SEQ ID NO:28)
```
I A V F P L L S A L I L I I L - (SEQ ID NO:27)

---

What is claimed is:

1. A method for assaying ghrelin O-acyltransferase (GOAT) activity in an in vitro, cell-free format comprising:
combining in vitro recombinant mammalian ghrelin O-acyltransferase, a ghrelin substrate of the acyltransferase, octanoyl-CoA, and a small molecule candidate agent, wherein the ghrelin substrate or the octanoyl moiety comprises a label, whereby the acyltransferase catalyses the covalent transfer of the octanoyl of the octanoyl-CoA to the ghrelin substrate to form labeled octanoyl-ghrelin substrate; and
isolating and quantifying the labeled octanoyl-ghrelin substrate to specifically determine the amount of acylation of the ghrelin substrate by the acyltransferase in the presence of the agent.

2. The method of claim 1 wherein the ghrelin substrate comprises the label.

3. The method of claim 1 wherein the octanoyl moiety comprises the label.

4. The method of claim 1 wherein the labeled octanoyl-ghrelin substrate is isolated by specifically immobilizing its octanoyl moiety.

5. The method of claim 1 wherein the labeled octanoyl-ghrelin substrate is isolated by specifically immobilizing its ghrelin substrate moiety.

6. The method of claim 1 wherein the label is a radiolabel.

7. The method of claim 1 wherein the label is a fluorescent label.

8. The method of claim 1 wherein the ghrelin substrate is ghrelin.

9. The method of claim 1 wherein the ghrelin substrate is pro-ghrelin.

10. The method of claim 1, wherein the acyltransferase is in membrane-bound form.

11. The method of claim 1, wherein the acyltransferase is in detergent-solubilized form.

12. The method of claim 1, wherein a reduced amount of acylation of the ghrelin substrate by the acyltransferase in the presence of the agent indicates that the agent specifically inhibits the acyltransferase.

13. The method of claim 1, wherein the octanoyl moiety comprises the label, the labeled octanoyl-ghrelin substrate is isolated by specifically immobilizing its ghrelin substrate moiety, the label is a radiolabel, the ghrelin substrate is pro-ghrelin, the acyltransferase is in membrane-bound form, and a reduced amount of acylation of the ghrelin substrate by the acyltransferase in the presence of the agent indicates that the agent specifically inhibits the acyltransferase.

14. The method of claim 1 wherein the acyltransferase is mouse, rat, human, chimpanzee, bovine, or horse ghrelin O-acyltransferase (GOAT).

15. The method of claim 1 wherein the acyltransferase is human ghrelin O-acyltransferase (GOAT).

16. The method of claim 1 wherein the acyltransferase is mouse ghrelin O-acyltransferase (GOAT).

* * * * *